(12) United States Patent
Alfano et al.

(10) Patent No.: US 6,205,353 B1
(45) Date of Patent: Mar. 20, 2001

(54) TIME-RESOLVED OPTICAL BACKSCATTERING TOMOGRAPHIC IMAGE RECONSTRUCTION IN SCATTERING TURBID MEDIA

(75) Inventors: R. R. Alfano; Wei Cai, both of Bronx, NY (US); Melvin Lax, Summit, NJ (US)

(73) Assignee: Research Foundation of CUNY, New York, NY (US)

( * ) Notice: Subject to any disclaimer, the term of this patent is extended or adjusted under 35 U.S.C. 154(b) by 0 days.

(21) Appl. No.: 09/218,199

(22) Filed: Dec. 22, 1998

(51) Int. Cl.$^7$ .................................................. A61B 5/05
(52) U.S. Cl. ................................................... 600/476
(58) Field of Search ................................. 600/310, 322, 600/476, 477

(56) References Cited

U.S. PATENT DOCUMENTS

| | | |
|---|---|---|
| 5,371,368 | 12/1994 | Alfano et al. . |
| 5,555,885 * | 9/1996 | Chance ................................. 600/477 |
| 5,762,607 * | 6/1998 | Schotland et al. ................... 600/476 |
| 5,813,988 | 9/1998 | Alfano et al. . |
| 5,847,394 | 12/1998 | Alfano et al. . |
| 5,905,261 * | 5/1999 | Schotland et al. ................... 600/476 |

FOREIGN PATENT DOCUMENTS

WO96/26431 8/1996 (WO) .
WO98/42248 10/1998 (WO) .

* cited by examiner

*Primary Examiner*—William E. Kamm
(74) *Attorney, Agent, or Firm*—F. Chau & Associates, LLP

(57) ABSTRACT

A method for imaging objects in a highly scattering turbid medium, such as breast, brain, prostate in human body and clouds, smoke in atmosphere environment, using backscattered light. The method involves using a group of sources and detectors setting on same side of medium to generate a plurality of time-resolved intensity data of backscattered light from the medium. The inverse computation using a reconstruction algorithm, taking the measured data as input, produces a three-dimensional image map of the internal structure of a turbid medium. The invention teaches (1) developing an accurate analytical solution of the Boltzmann photon transport equation in a uniform infinite medium, and its extension to the case of a semi-infinite medium, which serves as a background Green's function for the forward model; (2) building a forward physical model of relationship between measurement of backscattered light and inhomogeneity structure of the medium; (3) designing an inverse algorithm for backscattering tomography; (4) designing experimental setups for breast tumor detection using backscattering tomography; (5) using fsec, psec, and nsec laser pulse with different wavelengths in the near infrared spectral region; and (6) using pico-second time gating system as detectors to collect time-slicing data.

43 Claims, 10 Drawing Sheets

TIME-RESOLVED OPTICAL BACKSCATTERING TOMOGRAPHIC IMAGE RECONSTRUCTION IN SCATTERING TURBID MEDIA

BACKGROUND

1. Technical Field

The present invention relates generally to the imaging of objects in highly scattering turbid media and, more particularly, to a novel optical backscattering tomographic technique using optical radiation in visible, near infrared (NIR) spectral region for imaging objects in highly scattering turbid media.

2. Description of Related Art

There are many situations in which the detection of objects in a highly scattering turbid medium using backscattered light is highly desirable. For example, backscattered light may be utilized to detect a tumor embedded within tissue, such as breast tissue. Another example is using a laser source and detector located in an aircraft or a satellite to monitor the earth's atmospheric structure, such as cloud distribution, and land and water terrain. This method may also be used to detect hidden objects in a foggy or smoky environment. Various types of microscopes use backscattered light to display the surface image of a medium with high resolution. A confocal arrangement can extend the image to less than 200 $\mu$m below the surface.

The conventional Optical Coherent Tomography (OCT) technique, which uses backscattered light, can only image the internal structure of an eye and tissue down to about 600 $\mu$m below the skin surface. No clear image of the medium structure in a deeper depth, however, can be formed using the direct backscattered light signals. This is due to multiple light scattering within a medium, which contributes to noise, loss of coherence, and reduces the intensity of light directly backscattered from the hidden object.

Presently, diffusion optical tomography is a widely utilized optical image reconstruction tomographic technique. Examples of references which disclose this technique include: U.S. Pat. No. 5,813,988 to Alfano et al. entitled "Time-Resolved Diffusion Tomographic Imaging In Highly Scattering Turbid Media," which issued Sep. 29, 1998; W. Cai et al., "Time-Resolved Optical Diffusion Tomographic Image Reconstruction In Highly Scattering Turbid Media," Proc. Natl. Acad. Sci. USA, Vol. 93 13561–64 (1996); Arridge, "The Forward and Inverse Problems in Time Resolved Infra-red Imaging," Medical Optical Tomography: Functional Imaging and Monitoring SPIE Institutes, Vol. IS11, G. Muller ed., 31–64 (1993); and Singer et al., "Image Reconstruction of Interior of Bodies That Diffuse Radiation," Science, 248: 990–3 (1993), all of which are incorporated herein by reference.

The conventional diffusion optical tomography method has several disadvantages. For example, the diffusion method only uses diffusive photons which have suffered many scattering events. Therefore, the signals received by detectors are less sensitive to changes in the structure of the turbid medium, which makes it difficult to obtain high-resolution image reconstruction. Furthermore, the diffusion method requires that the source and detector be far enough apart such that diffusion is valid (e.g., larger than 5 $l_t$, where $l_t$ is the transport mean free path). This leads to non-portable, costly equipment (in contrast to the backscattering arrangement where the sources and the detectors can be set near each other). Indeed, in many important applications it is virtually impossible to arrange the source and the detectors separately. Another disadvantage to this approach is that it requires the simultaneous imaging of a large volume of the medium, which, in many cases, is the entire volume of the turbid medium being tested. When solving the inverse problem, however, due to practical limitations in computation time, the number of voxels (a voxel is a division of the medium) can not be too large since the computation time is proportional to $N^{2.5-3}$, where N is the number of voxels. In addition, imaging a large volume leads to a large volume of each voxel and low resolution. Consequently, the resolution obtained by using the conventional diffusion tomography method is on the order of a few centimeters.

The theoretical basis for diffusion tomography is the "diffusion approximation" to the more accurate Boltzmann photon transport equation. The above-mentioned disadvantages associated with diffusion tomography originate from failure of the "diffusion approximation" to describe the early-time migration of photons, which is when the photon distribution is highly anisotropic. Correspondingly, diffusion tomography can not be utilized in a backscattering arrangement, where sources and detectors are arranged near each other and, hence, early-time photon migration plays an important role.

SUMMARY OF THE INVENTION

It is an object of the present invention to provide a forward physical model of backscattering optical tomography for imaging objects in highly scattering turbid media.

It is another object of the present invention to provide an accurate analytical solution of the Boltzmann photon transport equation in an infinite uniform medium to serve as background Green's function in the forward physical model for the backscattering tomography method of the present invention.

It is another object of the present invention to provide a specific inverse algorithm (which is unique to the present backscattering tomography method) for determining the structure of a highly scattering turbid medium layer by layer to produce an internal map of the medium.

It is another object of the present invention to provide a tomographic method using laser sources with different wavelengths for producing an internal map of a specific material structure in a turbid medium.

It is another object of the present invention to provide experimental designs for using backscattering tomography for detecting breast cancer and to develop an optical mammography and/or tomography imaging system.

The present invention is directed to a novel optical backscattering tomographic method for imaging hidden objects in highly scattering turbid media. In one aspect of the present invention, a method for imaging objects in a highly scattering turbid medium includes the steps of: illuminating a highly scattering medium with light in visible and/or infrared spectral region; utilizing different time-gating techniques to acquire time-resolved signals of backscattered light emergent from the medium received by detectors located near the light source; applying an accurate physical model of photon migration based on solving the Boltzmann photon transport equation; and applying a specific inverse algorithm to form an image of the objects in the highly scattering turbid medium.

The optical inverse image reconstruction method of the present invention (which is based on knowledge of the physical principles of photon migration in a highly scattering turbid medium) utilizes a mathematical inverse algorithm to process intensity data of detected backscattered light to produce an image map of the internal structure the turbid medium. Advantageously, the deep internal structure of the turbid media can be imaged using the present method. For example, human tissue can be imaged to a depth on the order of several centimeters to tens of centimeters.

Preferably, an accurate analytical solution of the Boltzmann photon transport equation in an infinite uniform medium, first derived by the inventors, is described by equations (7) to (22) in the section of "detailed description of preferred embodiments".

Preferably, the aforementioned physical model of photon migration for backscattering tomography is formed as follows. The optical parameters in a turbid medium (having hidden objects) are $\mu_s(r)$ the scattering rate, $\mu_a(r)$ the absorption rate, and $\mu_s(r)P(s', s, r)$ the differential angular scattering rate. These parameters are position dependent, and represent the non-uniform structure of the highly scattering turbid medium. The values of these optical parameters change with different wavelength, $\lambda$, of light sources. We define a change of scattering and absorption parameters as follows:

$$\Delta \mu_s(r) = \mu_s(r) - \mu_s^{(0)};$$

$$\Delta \mu_a(r) = \mu_a(r) - \mu_a^{(0)};$$

and $$\Delta[\mu_s P](s', s, r) = \mu_s(r)P(s',s,r) - \mu_s^{(0)}P^{(0)}(s',s);$$

where the quantities with super index (0) are the optical parameters in a uniform background medium (a medium without hidden objects).

The physical model for photon migration for backscattering tomography based on the Born approximation is given by the following formulas:

$$\Delta I(r_d, s_d, t | r_s, s_s) = \int dt' \int dr \int ds' I^{(0)}(r_d, s_d, t-t' | r, s')$$

$$\{\int \Delta[\mu_s P](s', s, r) I^{(0)}(r, s, t' | r_s, s_s) ds - [\Delta \mu_s(r) + \Delta \mu_a(r)] I^{(0)}(r, s', t' | r_s, s_s)\}$$

where $\Delta I$ $(r_d, s_d, t | r_s, s_s)$ is the change in light intensity received by a detector located at $r_d$, along the direction $s_d$, and at time t, which is injected from a source located at $r_s$ along a direction of $s_s$, at time t=0. The word "change" refers to the difference in intensity compared to that received by the same detector, from the same source, but light passing through a uniform background medium (that is, the medium without the hidden objects). $I^{(0)}(r_2, s_2, t | r_1, s_1)$ is the intensity of light located at $r_2$ along the direction $s_2$ and at time t, which is injected from a position $r_1$ along a direction of $s_1$ at time t=0 migrating in a uniform background medium (that is, the medium without the hidden objects); its expression, first derived by inventors, will be given by equations (9) to (22) in the section "detailed description of preferred embodiments", when the sources and the detectors are immersed inside the medium. The more detailed description of the forward model is in the section "detailed description of preferred embodiments", equations (1) to (6).

Preferably, the aforementioned physical model is also applied for a semi-infinite medium (i.e., where the source and the detectors are located outside surface of medium) such that the expression for $I^{(O)}(r_2, s_2, t | r_1, s_1)$ is modified by adding a "virtual source."

Preferably, a novel inverse algorithm is specifically developed for the present optical backscattering tomography method, taking into consideration the fact that, with the backscattering method, the sources and detectors are located on the same side of the medium. Hence, time-resolved signals received by detectors before time t are all backscattered from a local region with depth d below the surface, where d is less than ct/2, and where c is the light speed in the medium. The algorithm first uses the signal data before an early time $t_1$ to inversely determine the structure of the first layer below the surface having a depth $d_1 < ct_1/2$. Then, using signal data received before time $t_2$ (which is larger than $t_1$) and using the previously obtained knowledge of the structure of the first layer, the structure of the second layer depth $d_2$ where $d_1 < d < d_2$ is inversely determined. By repeating the above process, the structures of deeper layers are, step by step, inversely reconstructed to obtain image of the medium.

In accordance with another aspect of the present invention, the present optical image method can be combined with a "medical knowledge catalog system." This system builds a relationship between the material components (for example, fat, tumor, blood, $H_2O$, ducts, glands, cysts, calcification regions, etc.) and their optical parameter values (e.g., the absorption coefficients and the differential angular scattering coefficients) at different light wavelengths. This system may also include other medical knowledge of the tissue structure. Based on optical parameters at a given layer or a position, obtained by inverse computation, and based on the wavelength of the light source, this system can determine what type of tissue structure should be at the given layer or position. Then, based on knowledge of optical properties of certain types of tissue structure, this system can correct and compensate the optical parameters obtained by direct inversion, thereby making these parameters more accurate. Based on these "corrected" optical parameters, one can further inversely obtain an accurate image for the next layers.

In addition, the catalog system can be used to determine the local material structure by distinguishing different values of optical parameters obtained by using different light wavelengths. For example, assume that fat has a strong absorption peak at a wavelength $\lambda_1$. When two sources are used having respective wavelengths $\lambda_0$ and $\lambda_1$, where $\lambda_0$ is a non-characteristic wavelength, the difference of their absorption coefficients can be obtained by inverse computation, $D(r) = \Delta \mu_a(r, \lambda_1) - \Delta \mu_a(r, \lambda_0)$. This process provides a significantly clearer image map of fat location by eliminating the background values. This procedure can yield maps of water, fat, blood, and calcification, even possibly cancer, using different $\lambda$.

In another aspect of the present invention, inverse methods combining a Fourier transform inversion with a matrix inversion are used in the inversion algorithm. A method of pre-computing an inverse matrix can be introduced to speed the reconstruction computation. References which disclose certain of these techniques include U.S. Pat. No. 5,813,988 to Alfano et al., entitled "Time-Resolved Diffusion Tomographic Imaging in Highly Scattering Turbid Media"; "Time-Resolved Optical Diffusion Tomographic Image Reconstruction in Highly Scattering Turbid Media," by Cai et al., Proc. Natl. Acad. Sci. USA, Vol. 93 13561–64 (1996), W. Cai et al; and "Three Dimensional Image Reconstruction in Highly Scattering Media," SPIE Vol.2979, p241–248 (1997), which are all incorporated herein by reference. Preferably, the inverse algorithm is designed to reconstruct three-dimensional image by combining a one-dimensional matrix inversion with a two-dimensional Fourier transform inversion using a uniform distributed plane light source. This design makes the image reconstruction computation fast and stable.

There are many distinct advantages associated with the backscattering tomographic method of the present invention, which are not realizable when using the conventional diffusion tomography method to image objects embedded in highly scattering turbid media. For example, the present method is based on an analytical solution of the more accurate Boltzmann photon transport equation, which describes photon distribution not only as a function of spatial position (as is used in the conventional diffusion tomography method), but also as a function of the direction of photon propagation. Therefore, a more accurate image with increased resolution can be obtained. Furthermore, with the present backscattering tomography method, the sources and the detectors are arranged on the same side of the medium, typically near each other. Therefore, the equipment is more compact and portable, and can be applied in many cases in which the conventional diffusion tomography method can not be implemented.

Another advantage to the present backscattering tomography method allows inverse computation to be performed (separately and/or in parallel) for imaging different local parts of a highly scattering turbid medium. This significantly increases image resolution as compared to the conventional diffusion tomography method. By using the aforementioned inverse algorithm for backscattering tomography, the computation burden is significantly reduced while providing increased reconstruction quality.

A further advantage of the present backscattering tomography method is that it produces optical parameters (e.g., the scattering angular distribution parameters) which can not be obtained by the conventional diffusion tomography method. Consequently, the parameters obtained by backscattering tomography of the present invention provide a more characteristic description of the structure of a highly scattering turbid medium.

These and other objects, features and advantages of the present invention will become apparent from the following detailed description of preferred embodiments, which is to be read in connection with the accompanying drawings.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
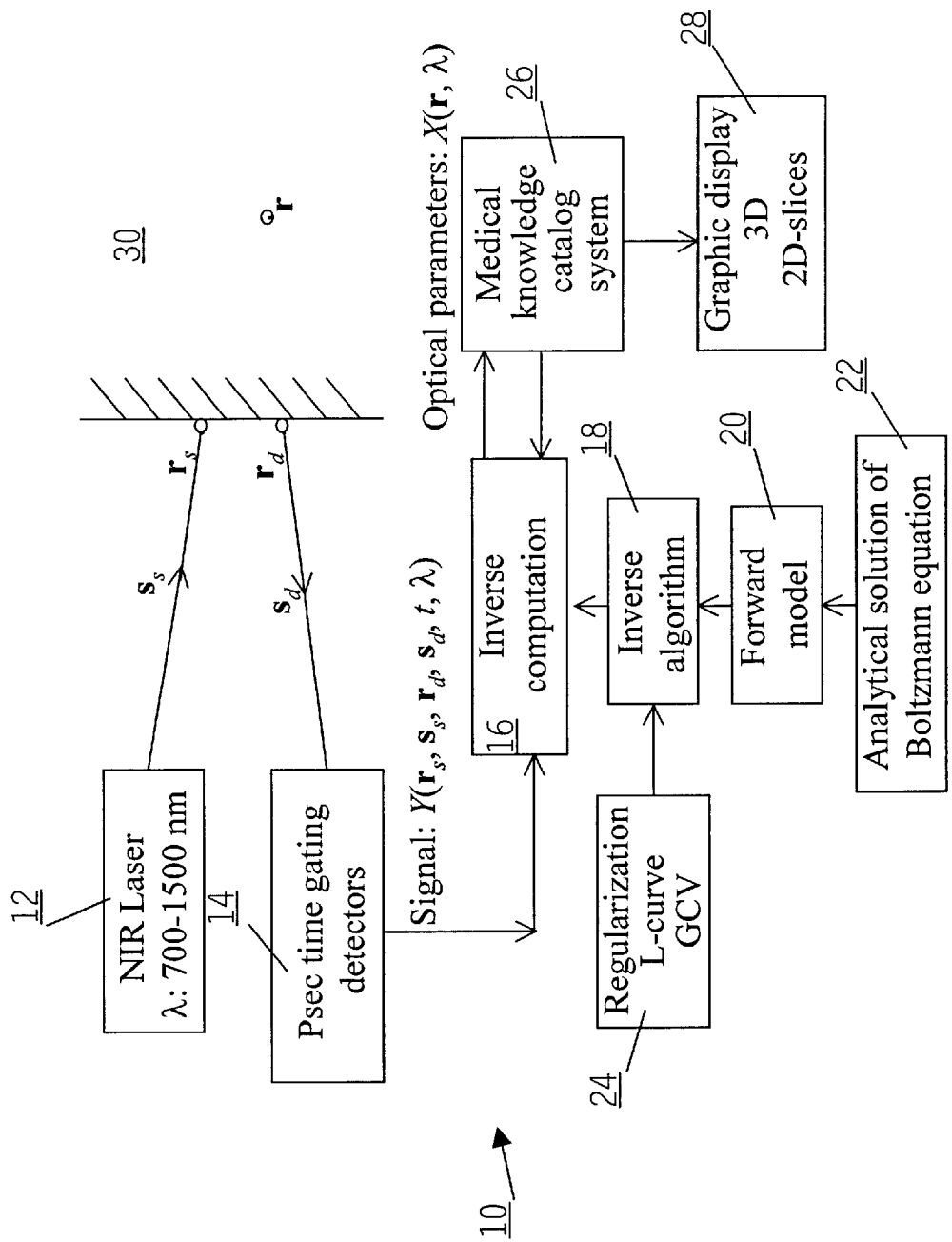
FIG. 1 is a block/flow diagram of an optical backscattering tomography system/process in accordance with an embodiment of the present invention.

The present invention is directed to novel optical backscattering tomographic system and method for imaging hidden objects in highly scattering turbid media. Referring now to FIG. 1, a block diagram illustrates an optical backscattering tomography system in accordance with one aspect of the present invention. It is to be understood that the block diagram depicted in FIG. 1 may also be considered as a flow diagram of a method for imaging objects in turbid media in accordance with the present invention. The system 10 includes an illumination source 12 for illuminating a turbid medium 30 with a pulse of light having a wavelength in the range of visible to near infrared spectral region. Preferably, the illumination source 12 is a laser which emits ultrashort light pulses (e.g., fsec, psec, and nsec pulses) having wavelengths in the range of about 700 to 1500 nm so as to obtain deep penetration of the turbid medium 30 (such as breast, prostate, and brain tissue). The laser source may include any conventional laser such as a Ti:Sapphire laser, a $Cr^{4+}$ Forsterite laser, a $Cr^{4+}$ YAG lasers, a $Cr^{4+}$—$Ca_2GeO_3$ (CUNYITE), a Nd:YAG laser, and a semiconductor laser.

A plurality of detectors 14 located near the source 12 are provided for acquiring time-resolved signals of backscattered light emergent from the turbid medium 30 using different time-gating techniques known to those skilled in the art. Preferably, the detectors 14 are implemented as a time gating Kerr or intensified CCD (charge coupled device) system for detecting pico-second time slicing signals. The resolution of time slicing is preferably on the order of $l_t/c$, where It is the transport mean free (which is about 1 to 4 mm in human tissue) and c is the light speed in the medium. In human tissue, the time slicing resolution is about 5 psec to 100 psec. The time-resolved light signals ("intensity data"), which are received by detectors 14, are intensity temporal profiles of the backscattered light at multiple time window/slices of the backscattered light. These profiles are functions of the position of the source 12 and detector 14, as well as the injecting direction of the source 12 and the receiving direction of the detector 14.

The intensity data which is detected and collected is processed via an inverse computation module 16 using a novel reconstructing algorithm to produce a three-dimensional image map of the internal structure of the turbid medium 30. Preferably, the intensity data used for producing an internal map of the turbid medium is collected, as discussed above, using time sliced photo-detectors with 10 psec to 200 psec time gated sliced images over 6000 psec. The reconstruction algorithm (which is utilized by the inverse computation module 16) includes a forward physical model 20. The forward model 20 (which is discussed in further detail below) describes photon migration (light propagation) in the turbid medium in accordance with optical parameters characteristic of a turbid medium: scattering rate, absorption rate, and differential angular scattering rate. The forward model 20 is based on an analytical solution 22 to the Boltzmann photon transport equation. Specifically, the analytical solution 22 comprises a cumulate solution of the Boltzmann photon transport equation in an infinite uniform medium and a corresponding solution in a semi-infinite uniform medium, by adding a virtual source. The analytical solution 22 serves as the background Green's function of the forward physical model 20 for the present backscattering tomography method.

An inverse algorithm module 18, which employs a novel inverse algorithm unique to the present imaging method, generates an internal map of the turbid medium by reconstructing the turbid medium structure layer by layer. The inverse process is discussed below in further detail.

Preferably, the reconstruction algorithm of the present invention includes a regularization module 24 which provides suitable regularization parameters for use by the inverse algorithm module 18. Conventional methods such as the L-curve method disclosed in "The Truncated SVD as a Method of Regularization," by Hansen, BIT, 17, 354–553, 1987, and the generalized cross validation (GCV) method disclosed in "Generalized Cross-Validation as a Method for Choosing a Good Ridge Parameter",by Golub et al, Technometrics, 21, p215–223 (1979), may be used in the regularization module 24 for providing suitable regularization parameters. These methods disclosed in these references are incorporated herein by reference.

The system 10 may also include a medical knowledge catalog system 26 for building a relationship between the different tissue structure and their corresponding optical parameters at different wavelengths of light source. The catalog system 26 is utilized by the inverse computation module 16 to determine the local tissue structure and refine the corresponding optical parameters at a position. This system 26 can be utilized to determine the local material structure by distinguishing or determining the local material structure from the local optical parameters (as discussed in further detail below).

The reconstruction algorithm of the system 10 also includes an image graphic display module 28 for generating and displaying 3-D reconstructed images.

It is to be understood that the present system and method is preferably implemented on a fast speed computer, for example, PC or Silicon Graphic (SGI), for fast numerical computation and graphic display.

It is to be further understood that the present system and method may be used to image various highly scattering turbid media such as biological plant tissue, animal tissue, and human tissue. With regard to human tissue, for example, the present invention can be utilized to image breasts, brain, prostate, arteries, liver, kidney, bones in joints, calcification regions, and arthritis, fingers, arms, legs, feet, etc. The turbid media which may be imaged also includes cloud, fog, smog, dust, smoke, etc, as well as defects in semiconductors, ceramics, and dielectrics.

Forward Physical Model

The following discussion provides the theoretical basis for the present invention. The structure of a highly scattering turbid medium can be characterized by the following optical parameters: $\mu_s(r)$ the scattering rate; $\mu_a(r)$ the absorption rate; and $\mu_s(r)P(s',s,r)$ the differential angular scattering rate.

These parameters are position dependent, and represent the non-uniform structure of the highly scattering turbid medium. The values of these optical parameters vary using light sources with different wavelengths, $\lambda$. For instance, the absorption rate, $\mu_a(r)$ will vary with the wavelength because the absorption peak appears when the wavelength matches the difference of the energy levels of a specific molecular structure. In addition, the scattering rate, $\mu_s(r)$, and the differential angular scattering rate, $\mu_s(r)P(s',s,r)$ vary with the wavelength because these rates are related to $R/\lambda$, where R is the average radius of the scatterer.

The photon propagation in a medium is described by the photon distribution function, $I(r, s, t)$, namely, the photon density in a unit of solid angle as functions of time t, position r, and direction s. The mathematical equation governing photon propagation is the well-known Boltzmann photon transport equation:

$$\partial I(r,s,t)/\partial t + cs \cdot \nabla_r I(r,s,t) + \mu_a(r)I(r,s,t) = \mu_s(r)\int P(s,s',r)[I(r,s',t)-I(r,s,t)]ds' + \delta(r-r_0)\delta(s-s_0)\delta(t-0) \quad (1)$$

Figure 2:
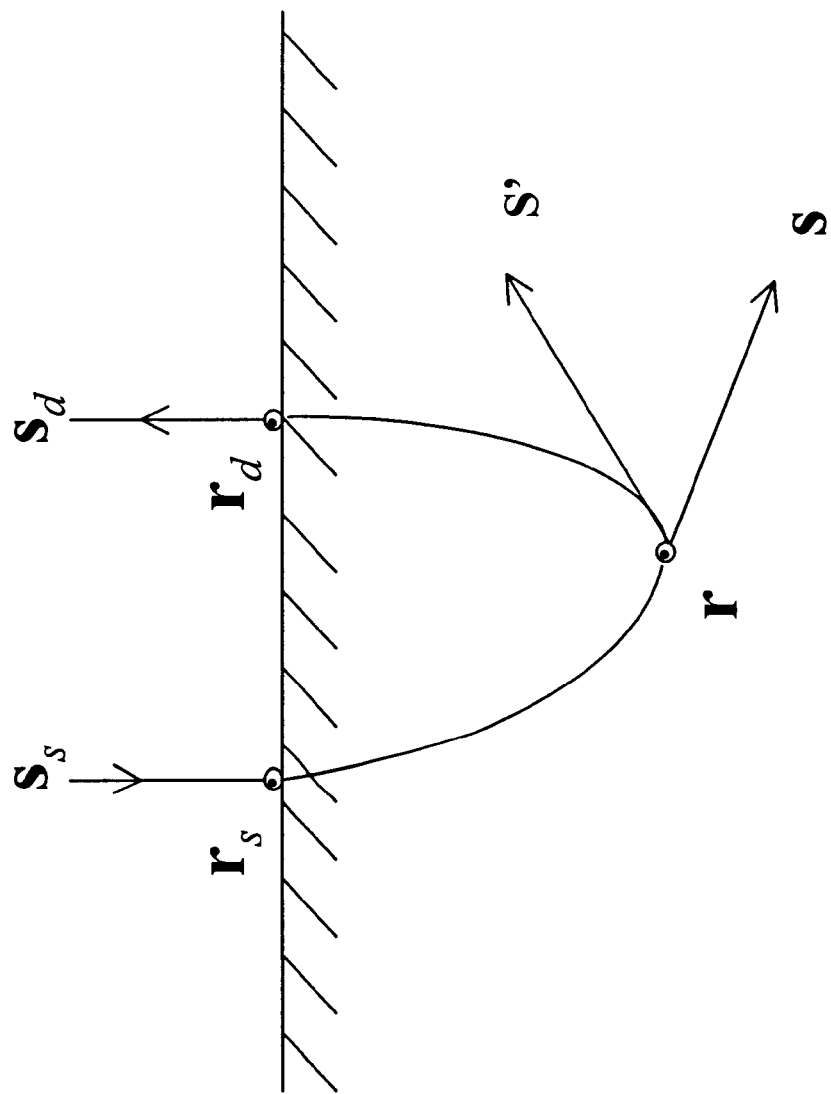
FIG. 2 is a schematic diagram of a forward optical backscattering model in accordance with one aspect of the present invention.

It is difficult to directly solve the above photon transport equation. Therefore, a perturbation method is used which designates the photon distribution function in a uniform background medium as the zero-order approximation. This method designates, as the first-order perturbation, the change of the photon distribution function due to the change of optical parameters compared to that in the uniform background medium. The change of scattering and absorption parameters are defined as follows:

$$\Delta\mu_s(r) = \mu_s(r) - \mu_s^{(0)};$$

$$\Delta\mu_a(r) = \mu_a(r) - \mu_a^{(0)}; \text{ and}$$

$$\Delta[\mu_s P](s', s, r) = \mu_s(r)P(s',s,r) - \mu_s^{(0)}P^{(0)}(s',s);$$

where the quantities with super index (0) are the optical parameters in a uniform background medium (i.e., a medium without hidden objects). By expanding $\Delta[\mu_s P](s',s,r)$ in Legendre polynomials, we get:

$$\Delta[\mu_s P](s', s, r) = \frac{1}{4\pi}\sum_l \Delta\mu_s(r)\Delta a_l(r)P_l[\cos(s's)] \quad (2)$$

with normalization of $\Delta a_0(r)=1$. The corresponding Legendre coefficients, $\Delta\mu_s(r)\Delta a_l(r)$ can also serve as optical parameters. The following equation based on the standard Born approximation method represents our forward model, schematically shown in FIG. 2:

$$\Delta I(r_d,s_d,t|r_s,s_s) = \int dt' \int dr \int ds' T^{(0)}(r_d,s_d,t-t'|r,s')$$

$$\{\int \Delta[\mu_s P](s',s,r)I^{(0)}(r,s,t'|r_s,s_s)ds - [\Delta\mu_s(r)+\Delta\mu_a(r)]I^{(0)}(r, s',t'|r_s,s_s)\} \quad (3)$$

where $\Delta I$ $(r_d,s_d,t|r_s,s_s)$ is the change in light intensity received by a detector located at $r_d$, along the direction $s_d$, and at time t, which is injected from a source located at $r_s$, along a direction of $s_s$, at time t=0. The word "change" refers to the difference in intensity compared to that received by the same detector, from the same source, but light passing through a uniform background medium (i.e., a medium without hidden objects). The term $I^{(0)}(r_2,s_2,t|r_1,s_1)$ is the intensity of light located at $r_2$ along the direction $s_2$ and at time t, which is injected from a position $r_1$ along a direction of $s_1$ at time t=0 migrating in a uniform background medium.

We expand the background Green's function in equation (3) in spherical harmonics:

$$I^{(0)}(r, s, t' | r_s, s_s) = \sum_{l,m} A_{lm}(r, r_s, s_s, t')Y_{lm}^{(e)}(s) + \quad (4)$$

$$B_{lm}(r, r_s, s_s, t')Y_{lm}^{(o)}(s),$$

$$I^{(0)}(r_d, s_d, t-t' | r, s') = \sum_{l,m} C_{lm}(r, r_d, s_d, t-t')Y_{lm}^{(e)}(s') +$$

$$D_{lm}(r, r_d, s_d, t-t')Y_{lm}^{(o)}(s'),$$

where $Y_{lm}^{(e)}(\theta,\phi)=P_l^{(m)}(\cos\theta)\cos(m\phi)$ and $Y_{lm}^{(o)}(\theta,\phi)=P_l^{(m)}()(\cos\theta)\sin(m\phi)$, with $P_l^{(m)}(\cos\theta)$ the associated Legendre function.

By making analytical integration over s and s' in equation (3), we obtain the following forward model in a linear matrix form:

$$Y=WX \quad (5)$$

wherein $Y=[\Delta I/I^{(O)}]$ has M elements, corresponding to measurements of light intensity with different $r_s$, $r_d$, $s_s$, $s_d$, and time t, and where X represents the change of optical parameters at different positions in the medium and includes $N=(L+2)K$ elements, where K is number of voxels, corresponding to the different positions in medium, and L is the cut-off value in the Legendre expansion in equation (2). The corresponding parameters are: $X_l(r)=\Delta\mu_s(r)\Delta a_l(r)/(2l+1)$, $l=1, 2, \ldots L$ (which are related to the differential angular scattering coefficients); $X_{L+1}(r)=-\Delta\mu_s(r)$ (which is related to the scattering coefficients); and $X_{L+2}(r)=-\Delta\mu_a(r)$ (which is related to the absorption coefficients). W is an MXN matrix. The elements, related to $l=1, \ldots L$, are given by:

$$W(r_d, s_d, r_s, s_s, t | l, k) = \quad (6)$$

$$\frac{\Delta V_k}{I^{(0)}(r_d, s_d, t | r_s, s_s)} \int_0^t dt' \sum_m \frac{4\pi}{\eta_m(2l+1)} \frac{(l+m)!}{(l-m)!}$$

$$[A_{lm}(r_k, r_s, s_s, t')C_{lm}(r_k, r_d, s_d, t-t') +$$

$$B_{lm}(r_k, r_s, s_s, t')D_{lm}(r_k, r_d, s_d, t-t')]$$

where $\eta_m=1$, for $m=0$, or $\eta_m=2$, for $m=1, 2, \ldots 1$, and $\Delta V_k$ is the volume of $k^{th}$ voxel. The elements related to $X_{L+1}(r)=-\mu_s(r)$ are obtained by sum of right side of equation (6) over l with $l=1, \ldots LL$ (the $l=0$ term has be canceled with $\Delta a_0(r)=1$ term). The elements related to $X_{L+2}(r)=-\Delta\mu_a(r)$ are obtained by sum of right side of equation (6) over l with $l=0, 1, \ldots LL$. The cut-off value, LL, is not necessary to be equal to L.

By replacing $Y=[\Delta I/I^{(O)}]$ by $^{-1}\ln[I/I^{(O)}]$ in left side of equation (5), our model, to some extent, automatically includes higher order non-linear contribution. This procedure is usually called the Rytov approximation.

The Solution of the Boltzmann Equation in an Infinite Uniform Medium

In order to use the aforementioned forward model, we need an expression of the photon transport equation in an uniform background medium, $I^{(0)}(r_2,s_2,t|r_1,s_1)$. Accordingly, the following discusses a novel accurate solution of the Boltzmann photon transport equation in an infinite uniform medium in accordance with the present invention. This novel derivation is based in part on the work by A. Y. Polishchuk and R. R. Alfano, "Photon diffusion on the velocity sphere", Optical Letters, Vol. 21, p916 (1996); and U.S. Pat. No. 5,625,458 to Alfano et al. entitled "Method And System For Imaging Objects In Turbid Media Using Diffusive Fermat Photons", all of which are incorporated herein by reference.

The Boltzmann photon transport equation for an infinite uniform medium is similar to equation (1), but the optical parameters $\mu_s$, $\mu_a$, and P(s', s) are spatial independent.

We study the dynamics of the photon distribution in the velocity space, $F(s, s_0, t)$, on a spherical surface of radius 1. In an infinite uniform medium, the dynamics is independent of the spatial coordinates, because $\mu_s$, $\mu_a$, and P(s', s) are spatial independent and the translation invariance ensures that it is also independent of the source position. The kinetic equation for $F(s, s_0, t)$ is given by:

$$\partial F(s,s_0,t)/\partial t + \mu_a F(s, s_0,t) + \mu_s[F(s,s_0,t) - \int P(s,s')F(s',s_0,t)ds'] = \delta(s-s_0)\delta(t-0) \quad (7)$$

Assuming that the phase function depends on only the scattering angle, and that we can expand the phase function in Legendre polynomials, $$P(s, s') = \frac{1}{4\pi}\sum_l a_l P_l[\cos(ss')] \quad (8)$$

the exact solution of equation (7) can easily be obtained:

$$F(s, s_0, t) = \sum_l \frac{2l+1}{4\pi}\exp(-g_l t)P_l[\cos(ss_0)]\exp(-\mu_a t) \quad (9)$$

where $g_l = \mu_s[1-a_l/(2l+1)]$. Two special values of $g_1$ are: $g_0=0$ and $g_1=c/l_t$, where $l_t$ is the transport mean free path. Equation (9) serves as the Green's function of light propagation in velocity space. In fact, in an infinite uniform medium, this propagator determines all behaviors of light migration, including the spatial distribution. The distribution function $I(r, s, t)$ (the source is located on $r_0=0$) is given by $$I(r, s, t) = \left\langle \delta\left(r - c\int_0^t s(t')dt'\right)\delta(s(t) - s)\right\rangle \quad (10)$$

We make a Fourier transform for the first $\delta$-function in equation (10) and make a cumulant expansion to the second order, $\langle e^A \rangle = e^{\langle A \rangle}e^{\langle AA/2 \rangle c}$, with $\langle AA \rangle c = \langle AA \rangle - \langle A \rangle\langle A \rangle$, which is the only approximation used in our calculation. We have $$I(r, s, t) = F(s, s_0, t)\frac{1}{(2\pi)^3}\int dk \exp\left\{ik_\alpha\left(r_\alpha - c\left\langle\int_0^t dt' s_\alpha(t')\right\rangle\right) - \quad (11)\right.$$

$$\frac{1}{2}k_\alpha k_\beta c^2\left(\left\langle\int_0^t dt'\int_0^t dt'' T[s_\alpha(t')s_\beta(t'')]\right\rangle - \right.$$

$$\left.\left.\left\langle\int_0^t dt' s_\alpha(t')\right\rangle\left\langle\int_0^t dt'' s_\beta(t'')\right\rangle\right)\right\}$$

where T denotes time-ordered multiplication, and $$\left\langle\int_0^t dt' s_\alpha(t')\right\rangle = \quad (12)$$

$$\frac{1}{F(s, s_0, t)}\int_0^t dt' \int ds' F(s, s', t-t')s'_\alpha F(s', s_0, t').$$

$$\left\langle \int_0^t dt' \int_0^t dt'' T[s_\alpha(t')s_\beta(t'')] \right\rangle = \qquad (13)$$

$$\frac{1}{F(s,s_0,t)} \left\{ \int_0^t dt' \int_0^t dt'' \int ds' \int ds'' F(s,s',t-t')s'_\alpha \right.$$
$$\left. F(s',s'',t'-t'')s''_\beta F(s'',s_0,t'') + t.c \right\}$$

where t.c. means the second term is obtained by exchanging the index $\alpha$ and $\beta$ in the first term. The integrations in equations (11), (12), and (13) are straightforward. In the following, we set $s_0$ along the z direction and denote s as $(\theta,\phi)$.

Our solution is given by $$I(r,s,t) = \qquad (14)$$

$$\frac{F(s,s_0,t)}{(4\pi)^{3/2}} \frac{1}{(detB)^{1/2}} \exp\left[-\frac{1}{4}(B^{-1})_{\alpha\beta}(r-r^c)_\alpha(r-r^c)_\beta\right]$$

with the center of the packet located at $$r_z^c = G \sum_l A_l P_l(\cos\theta)[(l+1)f(g_l - g_{l+1}) + lf(g_l - g_{l-1})] \qquad (15.1)$$

$$r_x^c = G \sum_l A_l P_l^{(1)}(\cos\theta)\cos\phi[f(g_l - g_{l+1}) + f(g_l - g_{l-1})] \qquad (15.2)$$

where $G = c\exp(-\mu_a t)/F(s,s_0,t)$, $A_l = (1/4\pi)\exp(-g_l t)$, gi is defined after equation (9), and $$f(g) = [\exp(gt) - 1]/g \qquad (16)$$

$r_y^c$ is obtained by replacing $\cos\phi$ in equation (15.2) by $\sin\phi$.

$$B_{\alpha\beta} = cG\Delta_{\alpha\beta} - r_\alpha^c r_\beta^c/2 \qquad (17)$$

with $$\Delta_{zz} = \sum_l A_l P_l(\cos\theta)\left[\frac{l(l-1)}{2l-1}E_l^{(1)} + \right. \qquad (18.1)$$
$$\left. \frac{(l+1)(l+2)}{2l+3}E_l^{(2)} + \frac{l^2}{2l-1}E_l^{(3)} + \frac{(l+1)^2}{2l+3}E_l^{(4)}\right]$$

$$\Delta_{xx,yy} = \sum_l \frac{1}{2}A_l P_l(\cos\theta)\left[-\frac{l(l-1)}{2l-1}E_l^{(1)} - \frac{(l+1)(l+2)}{2l+3}E_l^{(2)} + \right. \qquad (18.2)$$
$$\left. \frac{l(l-1)}{2l-1}E_l^{(3)} + \frac{(l+1)(l+2)}{2l+3}E_l^{(4)}\right] \pm$$
$$\sum_l \frac{1}{2}A_l P_l^{(2)}(\cos\theta)\cos(2\phi)\left[\frac{1}{2l-1}E_l^{(1)} + \right.$$
$$\left. \frac{1}{2l+3}E_l^{(2)} - \frac{1}{2l-1}E_l^{(3)} - \frac{1}{2l+3}E_l^{(4)}\right]$$

where (+) corresponds to $\Delta_{xx}$ and (−) corresponds to $\Delta_{yy}$.

$$\Delta_{xy} = \Delta_{yx} = \sum_l \frac{1}{2}A_l P_l^{(2)}(\cos\theta)\sin(2\phi) \qquad (18.3)$$

$$\left[\frac{1}{2l-1}E_l^{(1)} + \frac{1}{2l+3}E_l^{(2)} - \frac{1}{2l-1}E_l^{(3)} - \frac{1}{2l+3}E_l^{(4)}\right]$$

$$\Delta_{xz} = \Delta_{zx} = \sum_l \frac{1}{2}A_l P_l^{(1)}(\cos\theta)\cos(\phi) \qquad (18.4)$$

$$\left[-\frac{2(l-1)}{2l-1}E_l^{(1)} + \frac{2(l+2)}{2l+3}E_l^{(2)} - \frac{1}{2l-1}E_l^{(3)} - \frac{1}{2l+3}E_l^{(4)}\right]$$

$\Delta_{yz}$ is obtained by replacing $\cos\phi$ in equation (I18.4) by sin+. In equations. (15.2), (18.1)–(18.4), $P_l^{(m)}(\cos\theta)$ is the associated Legendre function, and $$E_l^{(1)} = [f(g_l g_{l-2}) - f(g_l g_{l-1})]/(g_{l-1} - g_{l-1}) \qquad (19.1)$$

$$E_l^{(2)} = [f(g_l - g_{l+2}) - f(g_l g_{l+1})]/(g_{l+1} g_{l+2}) \qquad (19.2)$$

$$E_l^{(3)}[f(g_l - g_{l-1}) - t]/(g_l - g_{l-1}) \qquad (19.3)$$

$$E_l^{(4)} = [f(g_l - g_{l+1}) - t]/(g_l - g_{l+1}) \qquad (19.4)$$

A cumulant approximate expression for density distribution is obtained from $$N(r,t) = \left\langle \delta\left(r - \int_0^t s(t')dt'\right)\right\rangle$$

Notice that since $\int ds F(s,s',t) = \exp(-\mu_a t)$ we have:

$$N(r,t) = \frac{1}{(4\pi D_{zz}ct)^{1/2}} \frac{1}{4\pi D_{xx}ct} \qquad (20)$$
$$\exp\left[-\frac{(z-R_z)^2}{4D_{zz}ct}\right]\exp\left[-\frac{(x^2+y^2)}{4D_{xx}ct}\right]\exp(-\mu_a t)$$

with the center of photon migration located at:

$$R_z = c[1 - \exp(-g_1 t)]/g_1 \qquad (21)$$

and the corresponding diffusion coefficients are given by:

$$D_{zz} = \frac{c}{3t}\left\{\frac{t}{g_1} + \frac{3g_1 - g_2}{g_1^2(g_1 - g_2)}[1 - \exp(-g_1 t)] + \right. \qquad (22.1)$$
$$\left. \frac{2}{g_2(g_1 - g_2)}[1 - \exp(-g_2 t)] - \frac{3}{2g_1^2}[1 - \exp(-g_1 t)]^2\right\}$$

$$D_{xx} = D_{yy} = \frac{c}{3t}\left\{\frac{t}{g_1} + \right. \qquad (22.2)$$
$$\left. \frac{g_2}{g_1^2(g_1 - g_2)}[1 - \exp(-g_1 t)] + \frac{1}{g_2(g_1 - g_2)}[1 - \exp(-g_2 t)]\right\}$$

Distributions in equation (14) and equation (20) describe photon a "cloud" anisotropically spreading from a moving center, with time-dependent diffusion coefficients. At early time $t \to 0, f(g) \sim t$ in equation (16). From equation (15) and equation (21), the center moves as $cts_0$. $E^{(1-4)}$ in equation (19) and $\Delta_{\alpha\beta}$ in equation (18) at early time are proportional to $t^n$, with n>1. This result indicates the corresponding diffusion coefficient being zero at $t \to 0$. These results present a clear picture of nearly "ballistic" (coherent) motion at $t \to 0$. With increase of time, the center motion slows down, while the transverse spatial components, $r_{x,y}^c$, appear, and the diffusion coefficients increase from zero. This stage of photon migration is often called a "snake mode" (quasi-coherent), in which each photon, on average, has suffered a few collisions.

With increasing time, the $l^{th}$ Legendre component in equations (14), (15), and (18) exponentially decay with a rate related to $g_l$. The detailed decay rate, $g_l$, is determined by shape of the phase function. Generally speaking, very high $l^{th}$ components decay in a rate of the order of $\mu_s$, as long as its Legendre coefficient $a_l$ is distinctly smaller than $2l+1$. Even in the case that the phase function has a very sharp forward peak, for which there are non-zero al for very high $l^{th}$ rank, they are, usually, much smaller than $2l+1$. Therefore, for the distribution function at time t after the ballistic stage is over, a truncation in summation of l is available.

At large times, the distribution function tends to become isotropic. From equations (20) to (22) the photon density, at $t>>l_t/c$ and $r>>l_t$, tends towards the conventional diffusion solution with the diffusive coefficient $l_t/3$. Therefore, our solution quantitatively describes photon migration from nearly ballistic motion, to snake, and then to diffusive motion.

The second cumulant expansion is a standard method in statistics, which leads to a Gaussian distribution. If we examine the spatial displacement after each collision event as an independent random variable, $\Delta r_i$, the total displacement is $\Sigma \Delta r_i (I=1, \ldots N)$. The central limit theorem claims that if N is a large number, then the sum of N variables will have an essentially Gaussian distribution. In our case, this requires a time t much larger than $\tau_s = 1/\mu_s$, which is possibly much smaller than the transport mean free time, $l_t/c$. This condition is readily satisfied after the ballistic stage is over. Advantageously, our formula also presents the correct physical picture even at the early ballistic stage.

Extending the Solution to a Semi-Infinite Uniform Medium

In many applications such as the invivo image of breast, prostate, and brain, the sources and detectors are not immersed inside a medium, but are located external to the surface of the medium. If the size of the surface and the thickness of the medium are much larger than the distance between the source and the detector, a semi-infinite medium geometry is suitable for describing photon migration. A semi-infinite medium is defined as a medium occupying the $z>0$ space. The corresponding Green's function in the uniform background, $I^{(0)}(r_2, s_2, t|r_1, s_1)$, must be modified.

The boundary condition of a semi-infinite medium can be assigned such that on the surface $z_c = -\alpha l_t$, a ballistic distance with $\alpha = 0.6-0.7$, there are no photons being reflected back into the medium. By denoting s as $(\theta, \phi)$, the following expression is used for describing this boundary condition:

$$\left( \int_0^{2\pi} d\phi \int_0^{\pi/2} \sin\theta \, d\theta I(r,s,t) \right)_{z=z_c} = 0 \qquad (23)$$

Figure 4:
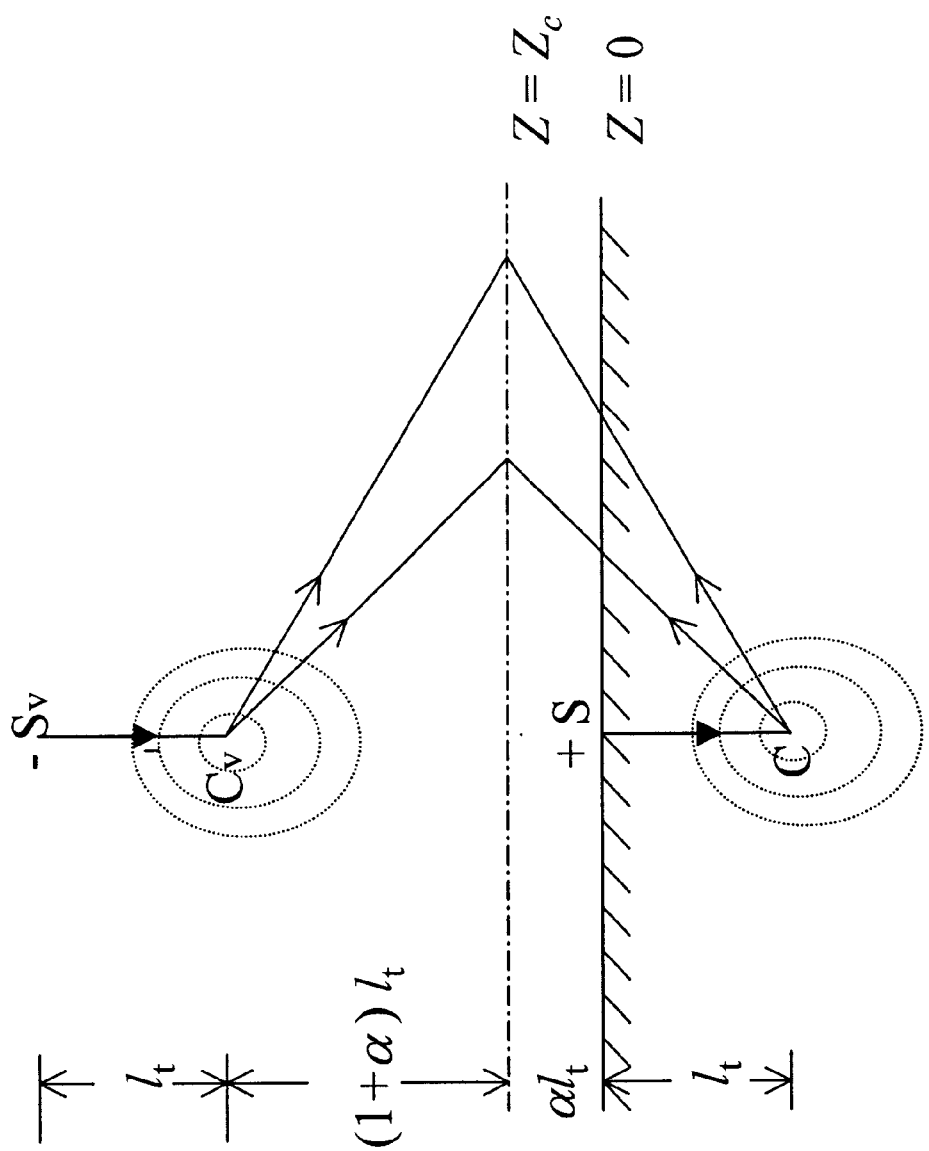
FIG. 4 is a graphic representation which illustrates the use of a virtual source to extend the solution of Boltzmann photon transport equation in a uniform infinite medium to that in a uniform semi-infinite medium.

As illustrated in FIG. 4, a virtual negative source, $S_v$, is added to the original source, S, to produce a solution approximately satisfying the above-mentioned boundary condition. This approach is similar to the method of adding a virtual source in diffusion tomography with semi-finite geometry. During the early period, the aforementioned solution of the Boltzmann equation in an infinite uniform medium automatically satisfies the boundary condition, and the virtual source plays no role. This is because the center of a "photon cloud" C moves nearly along positive z direction and the diffusion from the center is near zero. Therefore, the photon number at the surface above the medium is negligible at early time. After a lapse of time of approximately $l_t/c$, the center C stops at a position approximately $l_t$ from the original source S and the center from virtual source $C_v$ moves and stops at position approximately $l_t$ from the virtual sources $S_v$ (see equation (21)). Then, an approximate cancellation of contributions to the photon distribution is produced along positive z direction from the original source and the virtual source on the surface $z=z_c$.

In applying the aforementioned virtual source method for the Green's function $I^{(0)}(r_d, s_d, t-t'|r,s')$, an optical reciprocal theorem is also used:

$$I^{(0)}(r_d, s_d, t-t'|r, s') = I^{(0)}(r, -s', t-t'|r_d, -s_d) \qquad (24)$$

Inverse Algorithm for Backscattering Tomography

A novel inverse algorithm for optical backscattering tomography will now be discussed. This algorithm is predicated on the fact that with optical backscattering methods, the light sources and the detectors are located on the same side of the medium. Hence, the time-resolved signals received by detectors before time t are all backscattered from a local region within depth d below the surface, where d is less than ct/2, and where c is the light speed in the medium. Accordingly, the algorithm first uses the signal data before an early time ti to inversely determine the structure of the first layer below the surface having a depth $d_1 < ct_1/2$. Then, using the signal data before $t_2$, which is larger than $t_1$, and using obtained knowledge of the structure of the first layer, the structure of second layer with depth $d_1 < d < d_2$ can be inversely determined. In addition, the structures of deeper layers can be inversely reconstructed by repeating this method. This concept can be used to build an inverse algorithm based on any linear or non-linear forward model.

The inverse algorithm, which is based on the linear forward model using equation (5), is described as follows. The matrix equation (5) has the following structure:

$$\begin{bmatrix} Y(t_1) \\ Y(t_2) \\ Y(t_3) \\ \ldots \end{bmatrix} = \begin{bmatrix} W(d_1, t_1) & 0 & 0 & 0 \\ W(d_1, t_2) & W(d_2, t_2) & 0 & 0 \\ W(d_1, t_3) & W(d_2, t_3) & W(d_3, t_3) & 0 \\ \ldots & \ldots & \ldots & \ldots \end{bmatrix} \begin{bmatrix} X(d_1) \\ X(d_2) \\ X(d_3) \\ \ldots \end{bmatrix} \qquad (25)$$

where $X(d_i)$ are the parameters of the $i^{th}$ layer in the medium, $Y(t_j)$ are the measurements in the $j^{th}$ time range, $W(d_i, t_j)$ represents the contribution to the $j^{th}$ measurement from the $i^{th}$ layer. The elements in upper-right of the matrix are zero because the layers deeper than the $n^{th}$ layer do not contribute the measurements in and before the time range $t_n$.

According to the matrix structure shown in equation (25), we first inversely $Y(t_1) = W(d_1, t_1) X(d_1)$ to obtain $X(d_1)$. We then repeatedly perform the following procedures. First, by subtracting from $Y(t_j)$ the contributions from the previous layers, $\Delta Y(t_j)$ can be obtained, which is the contribution from the $j^{th}$ layer. Specifically, the following represents this:

$$\Delta Y(t_j) = Y(t_j) - \sum_{i<j} W(d_i, t_j) X(d_i).$$

Next, $\Delta Y(t_j) = W(d_j, t_j) X(d_j)$ is inversely solved layer by layer to obtain $X(d_j)$, $j=1, 2, 3, \ldots$ This optical image method (the inverse computation) can be combined with a "medical knowledge catalog system". This system builds a relationship between the material components (e.g., fat, $H_2O$, tumor, blood, ducts, glands, cysts, calcification regions, etc.) and their corresponding optical parameter values (e.g., the absorption coefficients, the scattering coefficients, and the differential angular scattering coefficients) at different light wavelengths. This system may also include other medical knowledge of the tissue structure. Based on the optical parameters at a given layer or position (which are obtained by inverse computation as discussed above) and the wavelength of the light source, this system is able to determine what kind tissue structure should be at the given layer or position. Then, based on the knowledge of optical properties of certain kinds of tissue structure, this system can correct and compensate the values of the optical parameters obtained by direct inversion, thereby making these parameters more accurate. Based on these "enhanced" optical parameters, one can further inversely obtain an accurate image for next layers.

Figure 5:
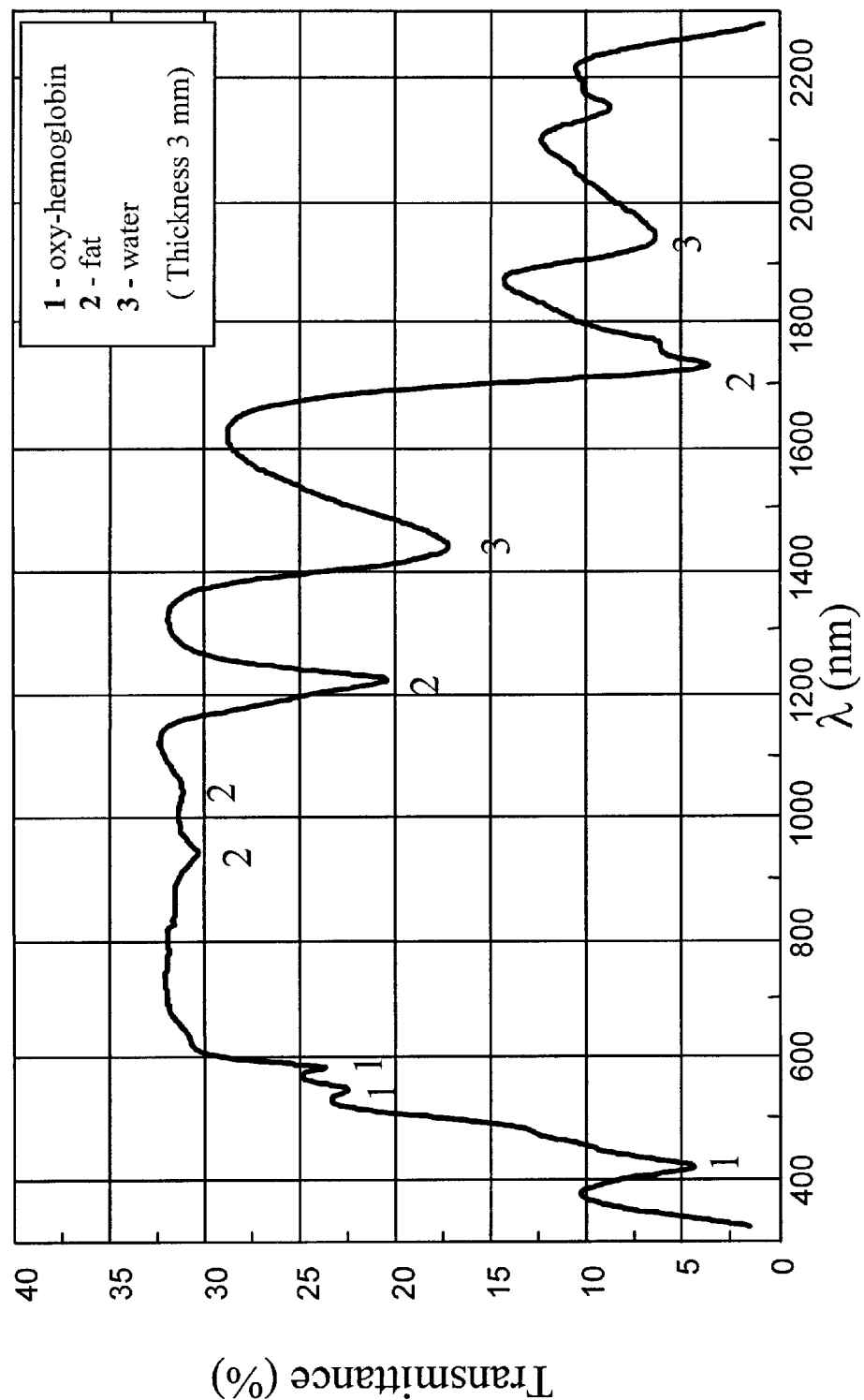
FIG. 5 is a graphical representation of the transmission spectrum in the visible to near infrared spectral region through a 3 mm thick slab of breast tissue, which illustrates absorption contributions from hemoglobin, fat, and water within the breast.
Figure 6:
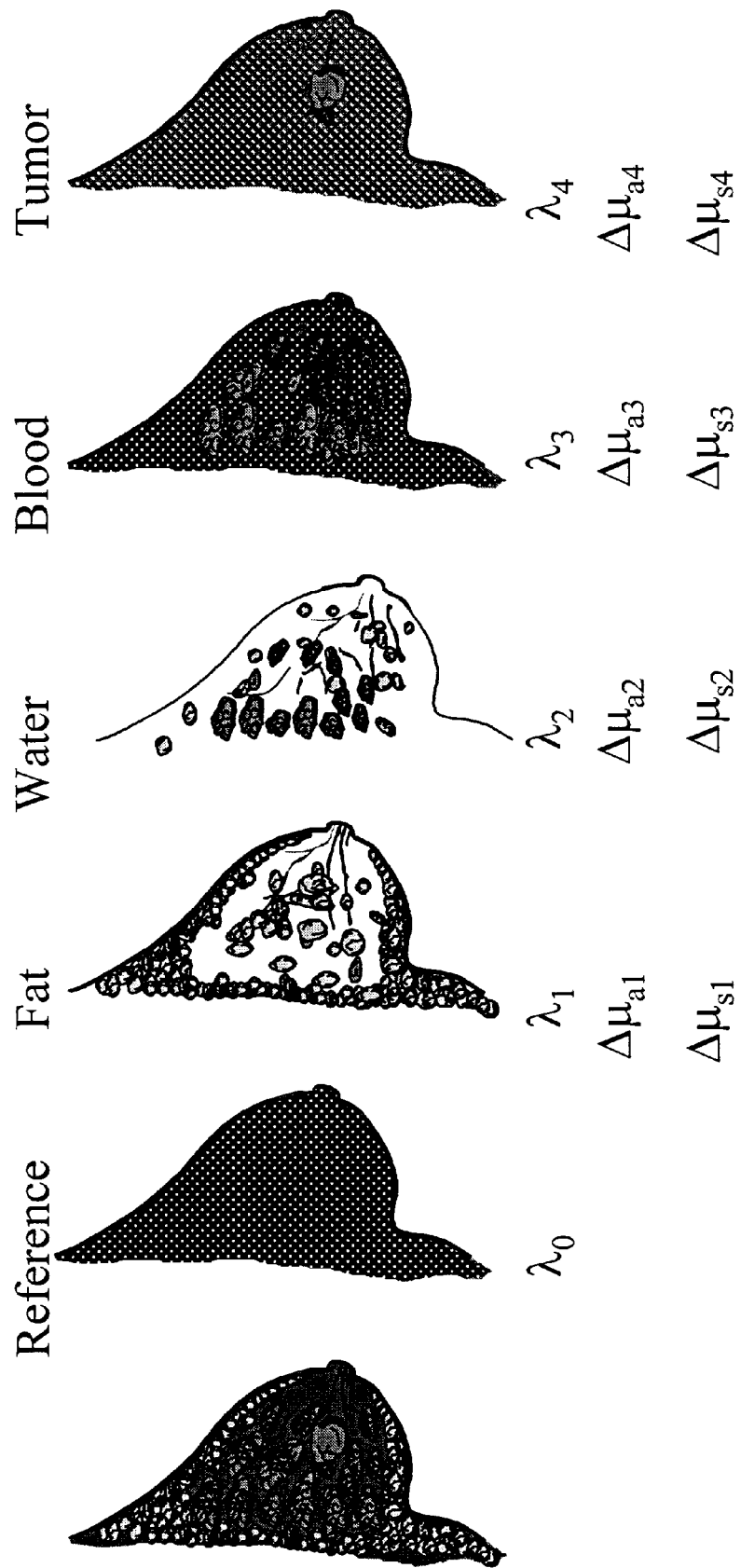
FIG. 6 is a schematic diagram illustrating image maps of key components of breast tissue using different wavelengths.

Advantageously, this system can determine the local material structure by distinguishing different values of optical parameters obtained using different light wavelengths. As shown in FIG. 5, absorption peaks appear at some special values of wavelengths, which corresponds to special breast structures. For example, fat has a strong absorption peak at a wavelength, $\lambda_1$, about 1200 nm (the publication which discloses this result includes F. A. Marks, "Physiological monitoring and early detection diagnostic method," Proc. SPIE 1641, p227–237, (1992), which is incorporated herein by reference). When two sources are used having wavelengths $\lambda_0$ and $\lambda_1$, where $\lambda_0$ is a non-characteristic wavelength, the difference of their absorption coefficients, obtained by our inverse computation, $D(r)=\Delta\mu_a(r,\lambda_1)-\Delta\mu_a(r,\lambda_0)$, shows a more clear image map where fat is located by eliminating the background values. A tumor developed inside fat on the other hand, has the absorption coefficients, at wavelength $\lambda_1$ less than that of surrounding fat. This procedure can yield maps of water, blood, and calcification using different $\lambda$.__A schematic diagram for using the different wavelengths in obtaining the internal maps of different components in a breast is shown in FIG. 6.

There are several advantages that are realized using this inverse algorithm First, this approach greatly reduces the computation time. Assuming N layers divide the medium, the computational time for the algorithm is proportional to N. In contrast the conventional computational time using a standard algorithm in inversely solving a matrix with size N is proportional to $N^{2.6}$ or $N^3$. Another advantage to using this approach is that images of layers from the surface of a medium to the deep region inside the medium are reconstructed step by step. Consequently, the inverse program can be terminated at a certain step, and an image of medium down to certain depth can be obtained. This is extremely useful in developing backscattering tomography, since the program may be checked, error may be estimated, and the image result may be analyzed at any step.

Experimental Design For Image of Breast

Figure 3C:
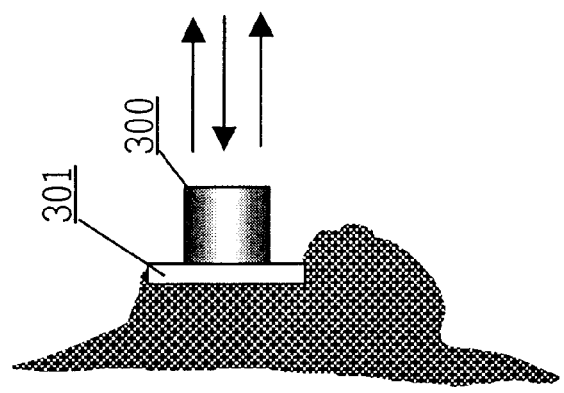
FIG. 3, parts (a), (b) and (c) are simplified schematic views of devices for detecting breast cancer using the backscattering tomography method of the present invention.
Figure 3B:
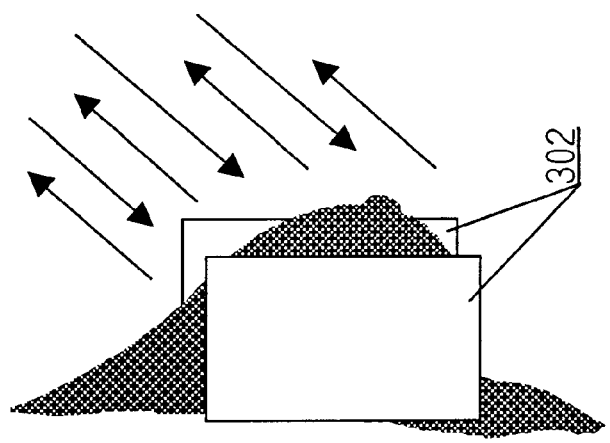
Figure 3A:
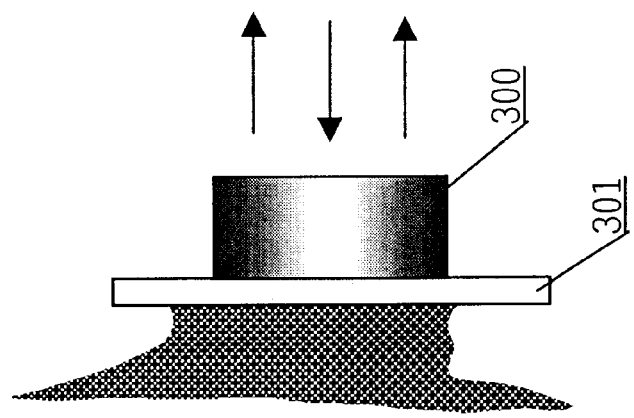

Referring now to FIG. 3, experimental devices are shown which may be utilized for detecting of breast cancer using optical backscattering tomography method of the present invention. As shown in FIG. 3 part (a), a source-detector head 300, which includes several sources and detectors, is fixed on a transparent plate 301. A medical doctor using a hand or other method (for example, moving the patient's bed) can press the plate 301 against a patient's breast to push the breast against the chest wall. Thereafter, a laser pulse can be applied, and the detectors can then record time-resolved backscattered light signals. From these signals, through numerical computation by computer using the backscattering tomography algorithm of the present invention, a three-dimensional image of the entire breast can be reconstructed. The breast is soft and flexible, it is possible to squeeze a breast to about 2 cm to 4 cm above the chest. In another embodiment as shown in FIG. 3 part (b), the breast may be squeezed between two parallel transparent plates 302. In addition, the embodiment shown in FIG. 3 part (c) can be used to detect a local breast region near the source-detector. The embodiment of FIG. 3 part (c) is similar to that shown in FIG. 3 part (a), but the source-detector head 300 and the plate 301 are smaller. By pushing successively upon different areas of the breast, a test of the entire breast can be completed. In order to reduce the clinic time, data acquisition can be performed during the visit with a patient. The image reconstruction then can be computed in parallel during the patient's waiting time. If a near real-time image reconstruction can be realized, the doctor may also see an image of the local region of patient's breast immediately after the laser beam is applied. Since only a local region of the breast is compressed (using the embodiment of FIG. 3 part (c), it is possible to push down the local region of breast to 1 cm to 2 cm above the chest wall using a moderate pressure. The advantage for the embodiments of FIG. 3 parts (a) and (b) is that the image of whole breast can be reconstructed at one time, hence, the clinic is fast. The embodiment of FIG. 3 part (c), on the other hand, can enhance the image resolution and can reduce pain because only a local region of breast is tested at a particular time.

Test of backscattering imaging method using simulating data

Figure 7:
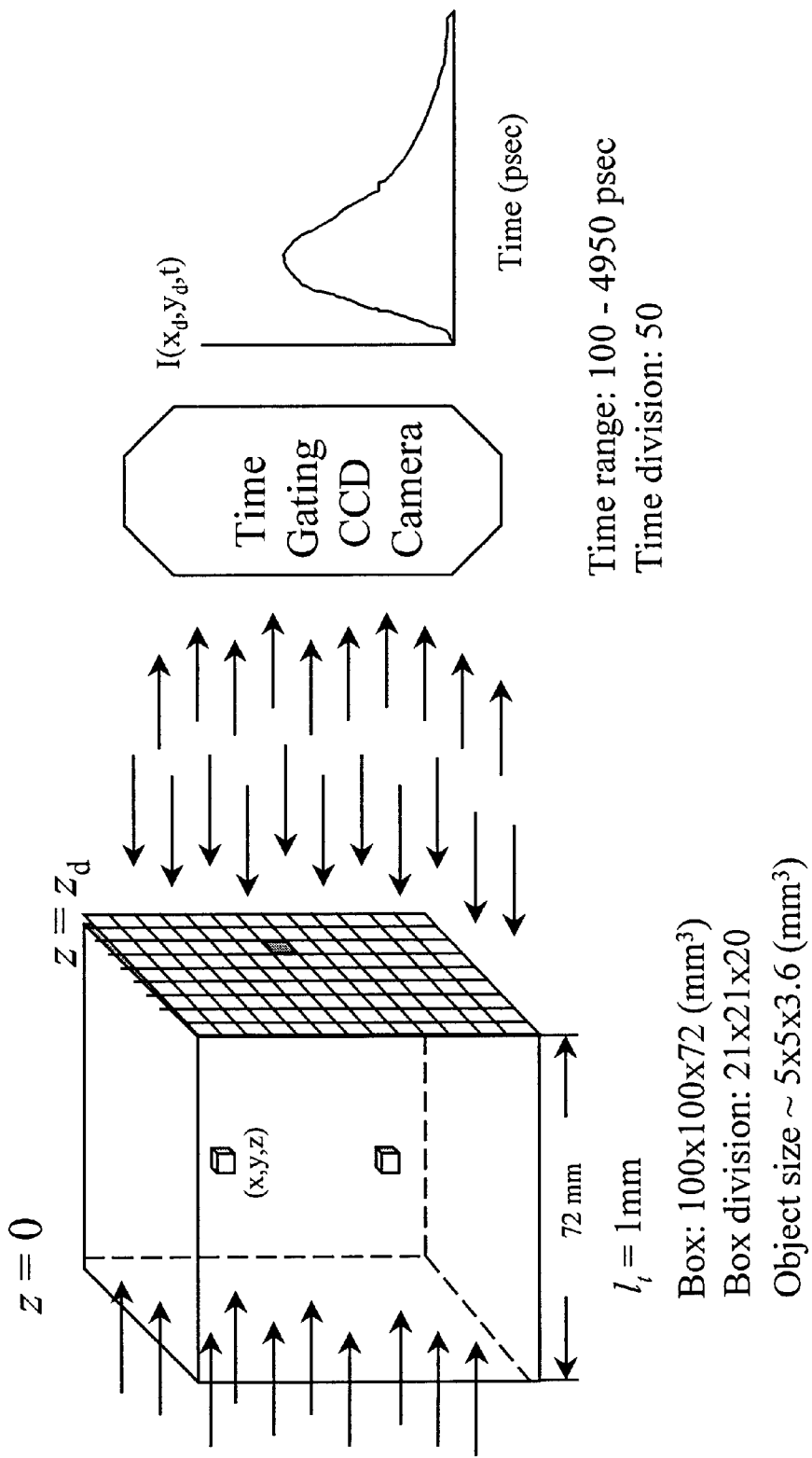
FIG. 7 is a diagram which illustrates an experimental design for testing the backscattering imaging method of the present invention to compare it with the conventional transmission (diffusion) imaging method.
Figure 8:
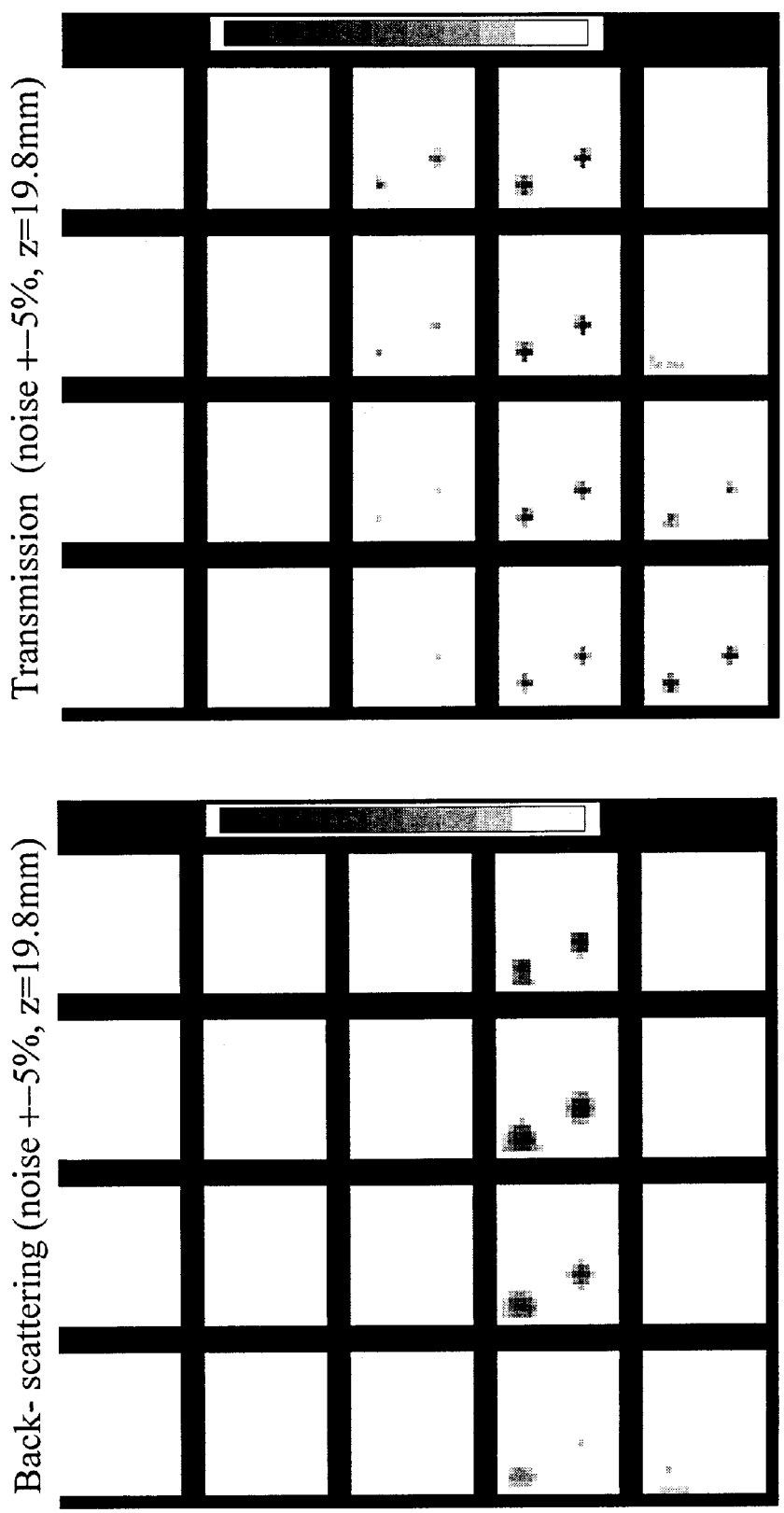
FIG. 8 is a diagram of comparative 3D images of two hidden objects located at 19.8 mm from a detector screen, using backscattering and transmission measurements with noise ±5%.
Figure 9:
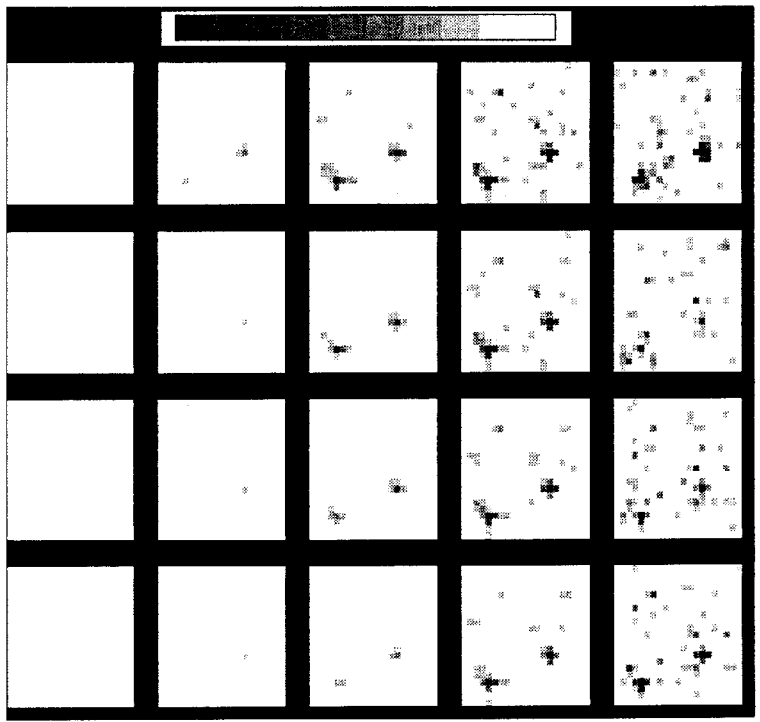
FIG. 9 is a diagram of comparative 3D images of two hidden objects located at 19.8 mm from a detector screen, using backscattering and transmission measurements with noise ±50%.
Figure 9:
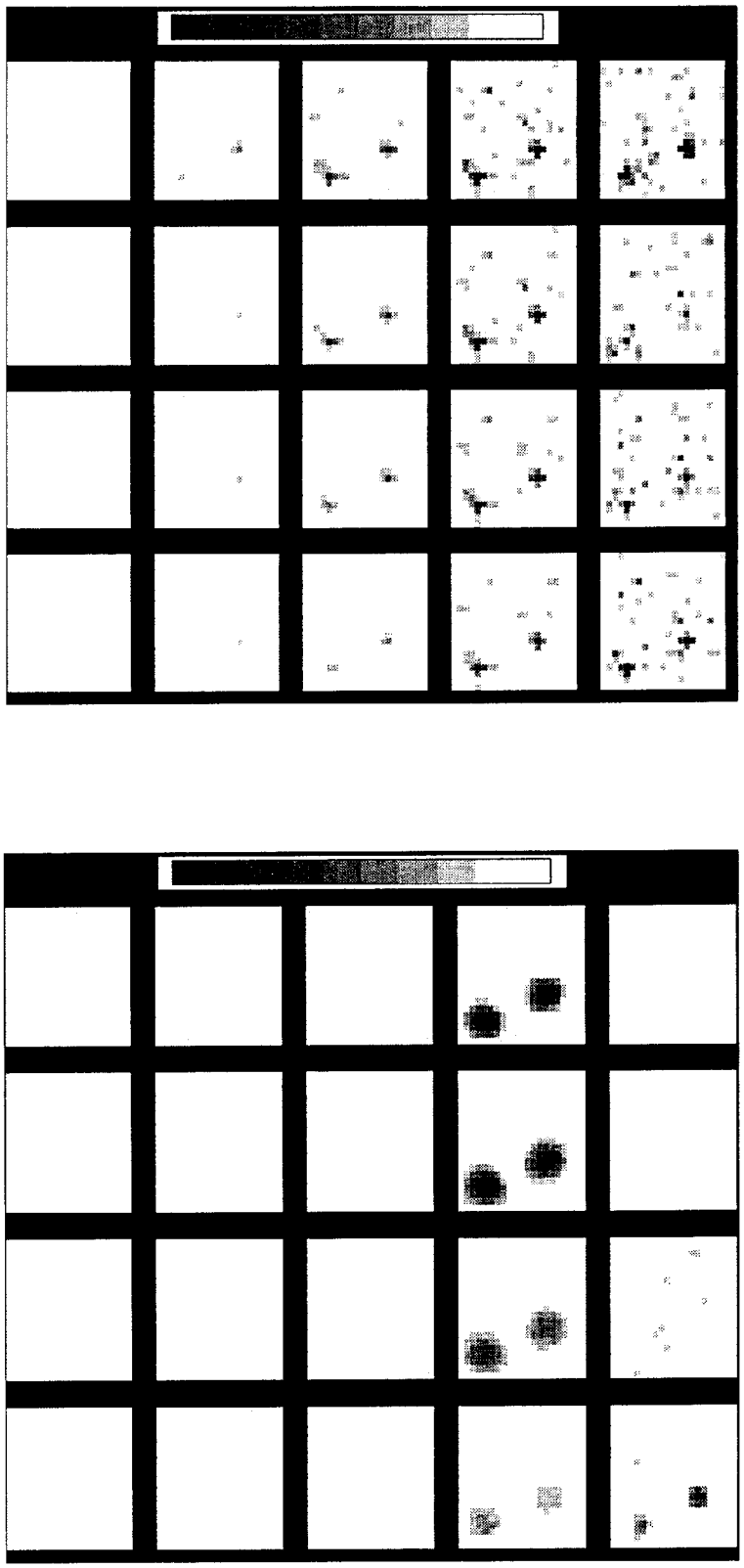
Figure 10:
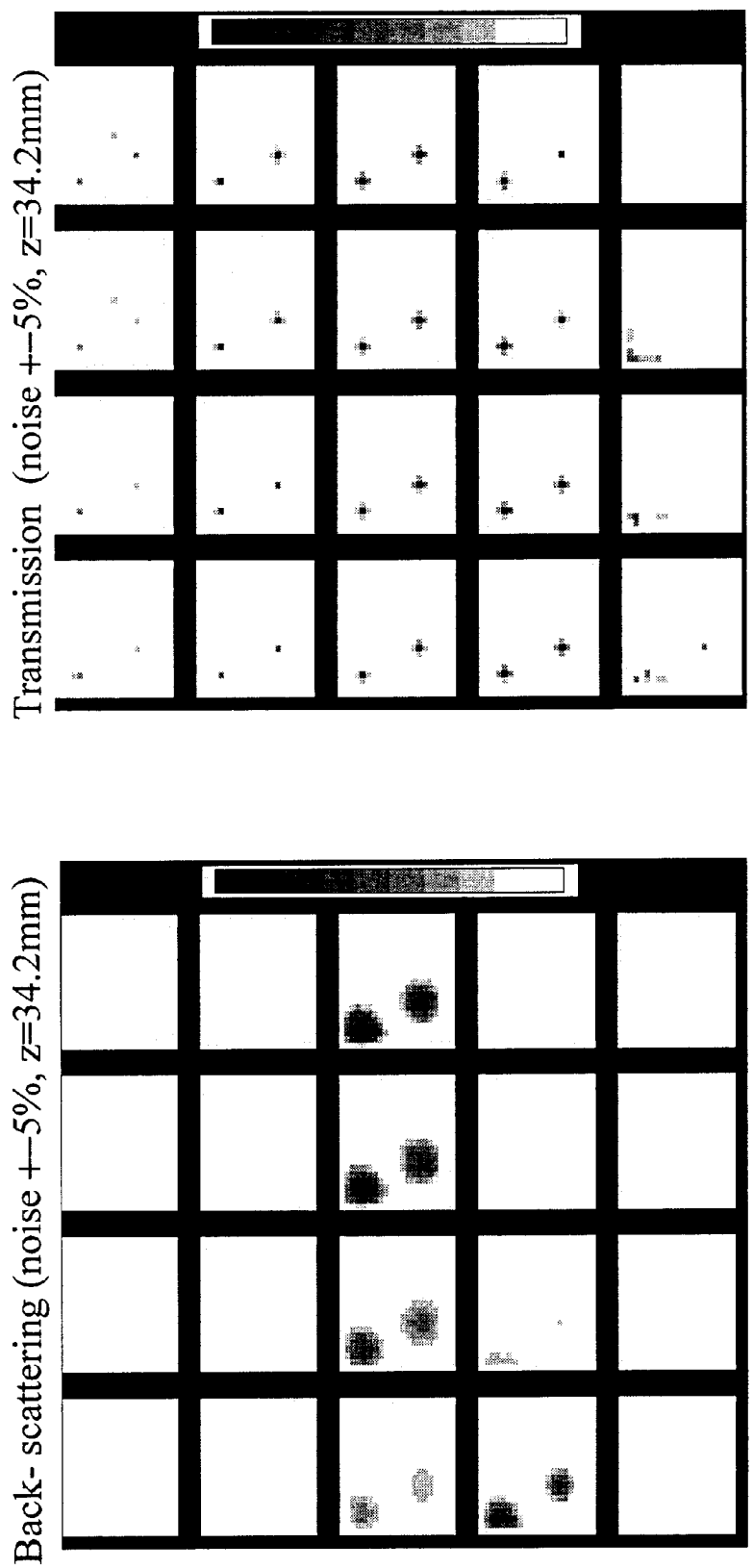
FIG. 10 is a diagram of comparative 3D images of two hidden objects located at 34.2 mm from a detector screen, using backscattering and transmission measurements with noise ±5%.

The advantages of the present backscattering imaging method as compared to the transmission imaging method will now be illustrated with reference to the experimental setup of FIG. 7 and simulation results of FIGS. 8–10.

The inverse algorithm of the conventional transmission imaging method is based on the diffusion approximation of the Boltzmann photon transport equation. This approximation is valid when the hidden objects are located at a distance from source and detectors which is significantly larger than the transport mean free path, $l_t$, which is suitable for the following experimental setup. The experimental setup illustrated in FIG. 7, is based on a slab geometry $(0, z_d)$ formed by Cartesian coordinates (x, y, z). A uniformly distributed plane source (theoretically, of infinite size) is located at z =0 plane for the transmission case or at $z=z_d$ for the backscattering case. The detector plane is located on $z=z_d$, and is mapped to a CCD camera through a lens. Using a time-gating system, the time-resolved intensity profiles, $I(x_d, y_d, t)$ can be obtained. The size on x-y plane is large enough, hence, the x-y boundary is assumed to be infinity. The background system is assumed to be uniform. Under the above-mentioned assumption, the Green's function related to the source is dependent only on z:

$$G^0(z, z_s, t) = \int_{-\infty}^{\infty} dx_s \int_{-\infty}^{\infty} dy_s G^0(x-x_s, y-y_s, z, z_s, t) \qquad (26)$$

The forward problem is represented as a matrix having the form as equation (5). For a time-resolved absorption tomography, W is written as:

$$W(x_d - x, y_d - y, z_d, z, t) = \qquad (27)$$
$$\frac{\Delta V}{G^0(z_d, z_s, t)} \int_0^t d\tau \frac{1}{4\pi Dc(t-\tau)} \exp\left\{\frac{-(x_d-x)^2 - (y_d-y)^2}{4Dc(t-\tau)}\right\} \times$$
$$G_z^0(z, z_d, t-\tau) G^0(z, z_s, \tau)$$

where $G_z^0(z, z_d, t)$ is a 1 D slab Green's function for background system with detector at $z_d$.

Under this experimental setup, a two-dimensional Fourier transform can be made over $x_d$-x and $y_d$-y to obtain $K_x \times K_y$ independent 1 D matrices, $W_{1D}(k_x, k_y)$, which are parameterized by $k_x$ and $k_y$. $W_{1D}(k_x, k_y)$ is a MxN matrix, where M is number of time slice, N is number of z division. The inverse algorithm for reconstructing the three-dimensional image combines a one-dimensional matrix inversion with a two-dimensional Fourier transform inversion by use of a uniform distributed plane light source. As is evident, the size of a 1 D matrix is much smaller, therefore, this approach will significantly increase both the speed and the quality of the image reconstruction.

A measurement region having a size $100 \times 100 \times 72 (mm^3)$ is divided to $21 \times 21 \times 20$. The uniform background medium has a transport mean free path, $l_t = 1$ mm, and an absorption length $l_a = 500$ mm. In each of the $21 \times 21$ simulated temporal profiles, intensities at 50 time slices uniformly distributed from 100 ps to 4950 ps were taken. Two absorptive hidden objects are located at (x, y) pixels (4,5) and (15, 18), and at different z positions, with an arbitrary unit of absorption coefficient. FIG. 8 illustrates 3-D images, separately, for the backscattering and transmission methods. The 20 consecutive squares represent the images on the different layers along the z-axis, counted from z=0 to $z=z_d$. Two hidden objects are located on the $15^{th}$ layer, namely 19.8 mm from the detector screen. The simulated time-resolved data are computed by adding uniformly distributed noise ±5%. FIG. 9 represents the images with the similar condition as that for FIG. 8, but adding uniform distributed noise ±50%. FIG. 10 represents the images with the similar condition as that for FIG. 8, but two hidden objects are located on 1 t layer, namely 34.2 mm from the detector screen.

FIGS. (8–10) show that the 3D images produced by the present backscattering method have much better quality than that produced by the conventional transmission method. In addition, the images produced by the present backscattering method have much better longitudinal resolution (resolution along z direction) and much higher noise-resistant ability as compared to that produced by the conventional transmission method.

In order to illustrate why the present backscattering method has the above-mentioned advantages as compared to the conventional transmission method, a one dimensional diffusion model with an absorptive object located in an infinite uniform background medium is analyzed. Analytically, it is proved that the change of intensity is independent of the position of the object, as long as the object is located between the source and the detector. This result hints a poor longitudinal sensitivity in optical diffusion tomography when transmission light is used.

The geometry of the problem can be described as follows. In an infinite uniform highly scattering turbid medium with the diffusion coefficient D, we set a plane source located on $-z_0$, and a plane detector on $z_0$. An absorptive board is inserted at $z:-z_0<z<z_0$, with the difference of absorption coefficient comparing with that of the background medium, $\Delta\mu_a$. The change of intensity due to inserting of the object is given by:

$$\Delta I(t, z) = S \Delta \mu_a c \Delta z \int_0^t d\tau G^0(z_0, z, t-\tau) G^0(z, -z_0, \tau) \quad (28)$$

where S is the strength of source, c is the speed of light in the medium, $\Delta z$ is the thickness of the object, and $G^0(z_2, z_1, t)$ is the ID Green's function in an infinite uniform medium:

$$G^0(z_2, z_1, t) = \frac{1}{(4\pi Dct)^{1/2}} \exp\left\{\frac{(z_1 - z_2)^2}{4Dct}\right\} \quad (29)$$

By introducing $u=\tau/t, \xi=z/z_0$, and $\alpha^2=z_0^2/DCt$, equation (28) is written as $$\Delta I(t, z) = (S \Delta \mu_a c \Delta z / 4\pi Dc) F(\xi, \alpha) \text{ with}$$

$$F(\xi, \alpha) = \int_0^t du \frac{1}{[u(1-u)]^{1/2}} \exp\left\{-\frac{\alpha^2}{4}\left[\frac{(1-\xi)^2}{(1-u)} + \frac{(1+\xi)^2}{u}\right]\right\}. \quad (30)$$

Denoting x=(2u/
x−1)/2[u(u−1)]$^{1/2}$, and in the case that $|\xi|<1$, we have $$F(\xi, \alpha) = \int_{-\infty}^{\infty} dx \frac{1}{(1+x)^2} \exp[-\alpha^2(1+x^2)]\left\{1 - \frac{\xi x}{(1+x^2-\xi^2)^{1/2}}\right\}. \quad (31)$$

The second term of the integrand in equation (31) is an odd function of x, hence, it contributes zero to the integration, and the first term contributes to $F(\xi,\alpha)=\pi[1-\text{erf}(\alpha)]$, where erf($\alpha$) is the error function, $$\text{erf}(\alpha) = 2/\pi^{1/2} \int_0^\alpha d\tau \exp(-\tau^2).$$

This result illustrates that $F(\xi,\alpha)$ is independent of $\xi$, and $\Delta I(t, z)$ is independent of z, the position of the absorptive plane. When a CW light source, or a frequency modulated light source, is used by integrating over t, or making a Fourier transform over t, one can reach the same conclusion: the change of intensity is independent of where the absorptive object is located. This poor longitudinal sensitivity, when the conventional transmission method is used, leads to not only low resolution in the image map of medium, but also making the inverse problem more ill-posed, hence, enhancing instability of the inversion solution at a certain signal to noise ratio. This poor longitudinal sensitivity is eliminated using the present backscattering method.

The following comments, observations, objects, features, uses, applications and/or advantages may be made about the present invention:

(1) The present backscattering tomography technique can be applied to different areas for image reconstruction of the internal structure of highly scattering turbid media. The present method may also be used in an earth environment and for cloud monitoring by setting the source and detector in an aircraft or satellites. Additionally, it may be used for safe, noninvasive breast screening and cancer detection by setting a source and detector on the surface of the breast.

(2) Intensity temporal profiles at multiple time window/slices of backscattered light are received by detectors which are located on the same side of the medium near the source. These profiles, as functions of positions and injecting/received directions of source and detector, are used as input data for inversely reconstructing the image of the medium.

(3) A novel image reconstruction algorithm for imaging in highly scattering turbid media using backscattering tomography is developed which comprises a physical model of light propagation in turbid media based on the Boltzmann photon transport equation, an inversion computation algorithm for reconstructing spatial distributions of key optical parameters of the turbid medium; a medical catalog expert system for determining the local material structure from the local optical parameters, and image graphic display.

(4) A cumulant solution of the Boltzmann photon transport equation in an infinite uniform medium and the corresponding solution in a semi-infinite uniform medium, by adding a virtual source, are derived, which serve as the background Green's function for the present backscattering tomography method.

(5) Key optical parameters, such as the scattering rate (transport length), the absorption rate (absorption coefficients), and the differential angular scattering rate, represented by its Legendre coefficients, are mapped for imaging the internal structure of a turbid medium. The difference of these parameters compared with that in a uniform background medium as functions of positions in the medium is obtained to form a 3D map of internal structure of the turbid medium. By using lasers with different wavelengths in near infrared spectral region, the quality of the imaging map can be enhanced.

(6) An inverse algorithm, specifically suitable for the present backscattering tomography method, is designed to perform image reconstruction layer by layer from the surface to a deep region inside the turbid medium.

(7) A "medical knowledge catalog system" builds a relationship between the different tissue structure and their corresponding optical parameters at different wavelengths of light source. This system is introduced in the inverse process to determine the local tissue structure and refine the corresponding optical parameters at a position. This system can determine the local material structure by distinguishing different values of optical parameters obtained using different light wavelengths.

(8) An inverse method, combining a Fourier transform inversion with a matrix inversion, can be used in the inversion algorithm. The method of pre-computing the inverse matrix can be introduced to speed the reconstruction computation. The L-curve method and the generalized Gross-validation (GCV) method can be used to choose suitable regularization parameters.

(9) Three-D images of the spatial distribution of the internal structure of the turbid medium, obtained using this algorithm, can be graphically displayed by 3-D graphic image or 2-D slice images.

(10) The present method may be used to image, noninvasively, invivo medical abnormalities in the human body, such as tumor growths in breasts, tumors in brain or prostate, cerebral hemorrhage in brain, blockage in arteries, hemorrhage in internal organs, breakage and calcification region, arthritis, in bones in joints, fingers, hands, arms, wrists, legs, feet, etc.

(11) Experimental devices for detecting breast tumors are designed for the present backscattering tomography method. These devices (shown in FIG. 3) use the characteristic of the breast (e.g., softness and flexibility) and a source-detector arrangement in the backscattering case to push the breast against the chest wall or to squeeze the breast between two transparent plates to produce images of either the entire breast or a local region(s) of the breast.

(12) The present method may be used with temporal data at various NIR wavelengths from 700 to 1500 nm for image reconstruction.

(13) The specific wavelength matching with the absorption peak of a certain human tissue structure is used for reconstructing the image map of the tissue structure. By subtracting the background value of the absorption coefficients obtained using non-characteristic wavelength, the resolution of the image map can be enhanced.

The embodiments of the present invention described above are intended to be merely exemplary and those skilled in the art should be able to make numerous variations and modifications to it without departing from the spirit of the present invention. All such variations and modifications are intended to be within the scope of the present invention as defined in the appended claims.

What is claimed is:

1. A method for imaging objects in a turbid medium using backscattered light, comprising the steps of:
   (a) illuminating said turbid medium with a pulse of light from a source;
   (b) receiving time-resolved backscattered light from said turbid medium by a plurality of time-gated detectors located near said source, said time-resolved signals providing intensity data as a function of received time, received direction, and detector position;
   (c) inversely constructing an image of said objects in said turbid medium by processing said intensity data using an image reconstruction algorithm including a forward physical model and an inverse algorithm.

2. The method of claim 1, wherein steps (a) and (b) are continuously repeated using sources with different positions and directions until data acquisition is complete.

3. The method of claim 1, wherein the step of inversely constructing said image includes the substeps of generating and displaying a graphical image.

4. The method of claim 1, further comprising the step producing an image of the structure of said turbid medium for different regions of said turbid medium by moving said source and detectors to different positions of the medium, and repeating steps (a) and (b) and (c) for each position.

5. The method of claim 1, further including the step of illuminating said turbid medium with a plurality of light sources having different NIR (near infrared) wavelengths.

6. The method of claim 1, wherein said forward physical model is based on a relation between a measurement signal and an optical parameter inhomogeneity of said turbid medium, wherein said measurement signal is a function of source position, source direction, detector position, detector direction and time, and said optical parameter inhomogeneity being the change in absorption rate, scattering rate, and differential angular scattering rate described by its Legendre coefficients, as compared to optical parameters in a uniform background medium.

7. The method of claim 6, wherein said forward physical model is based on an analytical solution to the Boltzmann photon transport equation.

8. The method of claim 7, wherein said analytical solution of the Boltzmann photon transport equation comprises a solution of the Boltzmann photon transport equation for a uniform infinite medium as described in equations (7) through (22) in the description of preferred embodiments, and an extension of the analytical solution for a uniform semi-infinite medium as described by equations (23) and (24) in the description of preferred embodiments.

9. The method of claim 7, wherein said analytical solution serves as a background Green's function in said forward physical model.

10. The method of claim 1, wherein said step of inversely constructing said image includes the substep of inversely reconstructing each successive layer of said turbid medium to produce an image of said turbid medium structure layer by layer from the surface of said turbid medium to a desired depth within said turbid medium.

11. The method of claim 10, wherein each successive layer is inversely reconstructed by subtracting the sum of the measured intensity data contributions from previous layers from the measured intensity data contributions at a desired layer to determine the intensity data contribution of the desired layer, and determining the optical parameters of the desired layer from said determined intensity data contribution of the desired layer to generate a map of the structure of the desired layer.

12. The method of claim 11, wherein said step of inversely reconstructing said image utilizes a one dimensional matrix inversion with a two dimensional Fourier transform inversion, whereby the reconstruction process speed in increased by precomputing the one dimensional inverse matrix image reconstruction.

13. The method of claim 1, wherein said pulse of light has a wavelength in the visible to near infrared region of the spectrum.

14. The method of claim 13, further comprising the steps of selecting said wavelength to match the absorption peak of a specific tissue structure and obtaining absorption coefficients using said selected wavelength.

15. The method of claim 13, further comprising the steps of selecting a second wavelength to match an absorption peak of a second structure, obtaining absorption coefficients with said second wavelength, and differentiating between said absorption coefficients obtained using said wavelength and said second wavelength to produce an image map for components of said specific tissue structure.

16. The method of claim 13, further comprising the steps of obtaining reference image data for breast tissue using a wavelength $\lambda_0$ having less absorption and computing an image of the breast tissue at other specific wavelengths for specific tissue structures including one of, $\lambda_1$ for fat, $\lambda_2$ for water, $\lambda_3$ for blood, and $\lambda_4$ for tumors and a combination thereof.

17. The method of claim 16, including the step of producing a three dimensional image using scattering and absorption optical properties said breast tissue for inversely reconstructing one of a three dimensional and two dimensional sliced image.

18. The method of claim 1, wherein the turbid medium is one of biological plant tissue, animal tissue and human tissue.

19. The method as claimed in claim 18 wherein said human tissue includes breast, brain, prostate, arteries, liver, kidney, and said objects include bones in joints, and calcification regions and arthritis in fingers, arms, legs, and feet.

20. The method of claim 1, wherein said turbid medium is one of cloud, fog, smog, dust, and smoke.

21. The method of claim 1, wherein said turbid medium is defects in semiconductors, ceramics, and dielectrics.

22. A system for imaging an object in a scattering turbid medium using backscattered light, comprising:
   illumination means for illuminating said turbid medium with a pulse of light;
   detection means, disposed near said source, for detecting time resolved backscattered light from said turbid medium using time-gating processing, said time-resolved signals providing intensity data as a function of received time, received direction, and detected position of said backscattered light signals;
   image reconstruction means for producing an image of said object in said turbid media by processing said intensity data using a physical forward model means and inverse algorithm means.

23. The system of claim 22, wherein said illumination means is a laser selected form the group consisting of Ti:Sapphire lasers, $Cr^{4+}$ Forsterite lasers, $Cr^{4+}$ YAG lasers, $Cr^{4+}$—$Ca_2GeO_3$ (CUNYITE), Nd:YAG lasers, and semiconductor lasers.

24. The system of claim 22, wherein said forward physical model is based on a relation between a measurement signal and an optical parameter inhomogeneity of said turbid medium, wherein said measurement signal is a function of source position, source direction, detector position, detector direction and time, and said optical parameter inhomogeneity being the change in absorption rate, scattering rate, and differential angular scattering rate described by its Legendre coefficients, as compared to optical parameters in a uniform background medium.

25. The system of claim 24, wherein said forward physical model is based on an analytical solution to the Boltzmann photon transport equation.

26. The system of claim 25, wherein said analytical solution of the Boltzmann photon transport equation comprises a solution of the Boltzmann photon transport equation for a uniform infinite medium as described in equations (7) through (22) in the description of preferred embodiments, and an extension of the analytical solution for a uniform semi-infinite medium as described by equations (23) and (24) in the description of preferred embodiments.

27. The system of claim 25, wherein said analytical solution serves as a background Green's function in said forward physical model.

28. The system of claim 24, wherein one of a Born approximation and a Rytov approximation is used to build said forward model.

29. The system of claim 24, wherein said a spherical harmonics expansion is used to analytically perform integration over the incident direction and the scattering directions on scatters.

30. The system of claim 22, wherein said inverse algorithm means operates to produce an image of the internal structure of the turbid medium layer by layer from the surface of said medium to a desired depth within said medium.

31. The system of claim 30, wherein said inverse algorithm means combines a Fourier transform inversion with a matrix inversion to reconstruct said image, wherein the inverse matrix inversion is precomputed to speed the reconstruction computation.

32. The system of claim 22, further including regularization means, operatively associated with said image reconstruction means, using one of an L-curve and a GCV method for selecting regularization parameters in said inverse reconstruction process to transfer an ill-posed problem to a well-posed problem.

33. The system of claim 22, further including a medical knowledge catalog system for building a relationship between the different tissue structure comprising the turbid medium and their corresponding optical parameters at different wavelengths of light source, said medical knowledge system operatively associated with said inverse reconstruction means for determining the local tissue structure, refining the corresponding optical parameters at a given position, and for determining the local material structure of said turbid medium by distinguishing different values of optical parameters obtained using different light wavelengths.

34. The system of claim 22, wherein said pulse of light has a wavelength in the visible to near infrared region of the spectrum.

35. The system of claim 34, wherein said pulse of light has a wavelength of about 700 nm to about 1500 nm.

36. The system of claim 34, wherein said pulse of light is an ultrashort pulse of light.

37. The system of claim 22, wherein said intensity data of said backscattered light signals are collected by detectors located at different positions, along different directions and at different time slicing.

38. The system of claim 37, wherein said time slicing signals are collected using time gating Kerr or time intensified gated CCD units.

39. The system of claim 37, wherein said detectors are time sliced photo-detectors with 10 psec to 200 psec time gated sliced images over 6000 psec to produce an internal maps of the scattering medium.

40. The system of claim 37 wherein the resolution of said time slicing is the order $l_t/c$, where $l_t$ is the transport mean free path and c is the light speed in the medium.

41. An experimental device incorporating the system of claim 22 to provide backscattering tomography for detecting breast tumors, wherein the device is able to test one of an entire breast and successively test different local regions of said breast.

42. The device of claim 41, including means for compressing the breast against the chest wall, and means for detecting backscattered light emergent from said breast for reconstructing an image of the breast.

43. The device of claim 42, wherein said compressing means includes two parallel transparent plates for compressing the breast therebetween.

* * * * *